United States Patent
Kilkenny et al.

(10) Patent No.: US 7,446,082 B2
(45) Date of Patent: Nov. 4, 2008

(54) CLEANING COMPOSITION FOR DISPOSABLE CLEANING HEAD COMPRISING A SULFAMIC ACID/ALKYL SULFATE SURFACTANT MIXTURE

(75) Inventors: Andrew Kilkenny, Pleasanton, CA (US); Maha Y. El-Sayed, Pleasanton, CA (US); Lafayette D. Foland, Pleasanton, CA (US); Shona L. Nelson, Pleasanton, CA (US); Cheryl Rodriguez, Pleasanton, CA (US); David R. Scheuing, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 11/737,957

(22) Filed: Apr. 20, 2007

(65) Prior Publication Data

US 2007/0191253 A1 Aug. 16, 2007

Related U.S. Application Data

(63) Continuation of application No. 10/758,722, filed on Jan. 16, 2004, now abandoned.

(51) Int. Cl.
*C11D 1/12* (2006.01)
*C11D 7/08* (2006.01)

(52) U.S. Cl. ............... 510/191; 510/199; 510/238; 510/253; 510/269; 510/362; 510/426; 510/427; 510/470; 510/477

(58) Field of Classification Search ........... 510/191, 510/199, 238, 253, 269, 362, 426, 427, 470, 510/477
See application file for complete search history.

(56) References Cited

U.S. PATENT DOCUMENTS

| | | | |
|---|---|---|---|
| 3,383,158 A | 5/1968 | Leland | |
| 3,413,673 A | 12/1968 | Gewirz | |
| 4,031,673 A | 6/1977 | Hagelberg | |
| 4,523,347 A | 6/1985 | Tames | |
| 4,852,201 A * | 8/1989 | Wundrock et al. | 15/145 |
| 5,003,659 A | 4/1991 | Paepke | |
| 5,140,717 A | 8/1992 | Castagliola | |
| 5,419,015 A | 5/1995 | Garcia | |
| 5,862,565 A | 1/1999 | Lundstedt | |
| 6,094,771 A | 8/2000 | Egolf et al. | |
| 6,217,889 B1 | 4/2001 | Lorenzi et al. | |
| 6,290,781 B1 | 9/2001 | Brouillet, Jr. | |
| 6,303,556 B1 * | 10/2001 | Kott et al. | 510/357 |
| 6,485,212 B1 | 11/2002 | Bomgaars et al. | |
| 6,569,261 B1 | 5/2003 | Aubay et al. | |
| 6,611,986 B1 | 9/2003 | Seals | |
| 6,716,805 B1 | 4/2004 | Sherry et al. | |
| 6,814,088 B2 | 11/2004 | Barnabas et al. | |
| 7,048,806 B2 | 5/2006 | Ochomogo et al. | |
| 2002/0002125 A1 * | 1/2002 | Colurciello, Jr. et al. | 510/238 |
| 2002/0007527 A1 | 1/2002 | Hart | |
| 2002/0187918 A1 * | 12/2002 | Urban | 510/505 |
| 2003/0070246 A1 | 4/2003 | Cavalheiro | |
| 2003/0100465 A1 | 5/2003 | Kilkenney et al. | |
| 2003/0216281 A1 * | 11/2003 | DeLeo et al. | 510/475 |
| 2004/0255418 A1 | 12/2004 | Minkler et al. | |
| 2005/0055787 A1 | 3/2005 | Blum et al. | |
| 2005/0066465 A1 | 3/2005 | Minkler et al. | |
| 2005/0079987 A1 | 4/2005 | Cartwright et al. | |
| 2005/0124519 A1 * | 6/2005 | Sherry et al. | 510/238 |
| 2005/0155628 A1 | 7/2005 | Kilkenney et al. | |
| 2006/0234899 A1 * | 10/2006 | Nekmard et al. | 510/439 |

* cited by examiner

*Primary Examiner*—Charles I Boyer
(74) *Attorney, Agent, or Firm*—David Peterson

(57) ABSTRACT

A cleaning implement with a handle and a removable cleaning pad can be used to effectively clean surfaces. The cleaning pad is impregnated with an acidic cleaning composition. The cleaning pad may be dry to the touch. The cleaning implement may be a manual tool or a motorized tool. Examples of suitable cleaning implements include a hard surface floor mop, a carpet mop, an auto cleaning device, a toilet cleaning device, a bathroom cleaning device, and a shower cleaning device.

13 Claims, No Drawings

CLEANING COMPOSITION FOR DISPOSABLE CLEANING HEAD COMPRISING A SULFAMIC ACID/ALKYL SULFATE SURFACTANT MIXTURE

BACKGROUND OF THE INVENTION

1. Field of the Invention

The present invention relates generally to devices for cleaning hard surfaces. The invention also relates to cleaning substrates, cleaning heads, cleaning pads, cleaning sponges and related systems for cleaning hard surfaces. The invention also relates to cleaning substrates, cleaning heads, cleaning pads, cleaning sponges and related systems for cleaning hard surfaces, wherein the cleaning substrates and related systems are impregnated with acidic cleaning compositions. The invention also relates to a device for cleaning hard surfaces that contains an onboard vessel containing an acidic cleaning composition. The invention also relates to a cleaning implement comprising a handle and a cleaning substrate, cleaning head, cleaning pad, cleaning sponge and related systems for cleaning hard surfaces. The invention also relates to a device for cleaning toilet bowls and the like. The invention also relates to a device for showers and bathtubs and the like.

2. Description of the Related Art

Numerous types of cleaning compositions, as well as holders for disposable cleaning pads, are known in the art. Illustrative are the compositions and apparatus disclosed in U.S. Pat. Nos. 4,852,201, 4,523,347, 4,031,673, 3,413,673 and 3,383,158.

U.S. Pat. No. 4,852,201 discloses a toilet bowl cleaner having a handle with a removable cleaning pad disposed on one end. The toilet bowl cleaner also includes a cleaning solution that is contained in the pad.

It is therefore an object of the present invention to provide a device with a disposable cleaning head that overcomes the disadvantages and shortcomings associated with prior art cleaning substrates, cleaning heads, cleaning pads, cleaning sponges and related systems for cleaning hard surfaces.

SUMMARY OF THE INVENTION

In accordance with the above objects and those that will be mentioned and will become apparent below, one aspect of the present invention comprises a cleaning implement comprising:

a. a handle; and
b. a removable cleaning pad comprising:
   i. 25 to 84% of a substrate selected from a group consisting of water-insoluble substrates, water-soluble substrates, and water-dispersible substrates, and combinations thereof; and
   ii. 16 to 75% of a cleaning composition impregnated in said substrate; wherein said cleaning composition comprises:
      1. 0 to 60% of an anionic surfactant;
      2. 0 to 60% of a nonionic surfactant; and
      3. 1 to 60% of a carboxylic acid selected from a group consisting of sulfamic acid, glycolic acid, lactic acid, citric acid, and combinations thereof, wherein said composition contains less than about 85% water.

In accordance with the above objects and those that will be mentioned and will become apparent below, another aspect of the present invention comprises A process of cleaning a shower using a cleaning implement with a disposable substrate impregnated with a cleaning composition comprising the steps of:

a. attaching said disposable substrate impregnated with said cleaning composition to said cleaning implement;
b. wetting the surface of said disposable substrate;
c. scrubbing the surface of said shower;
d. optionally, rewetting said disposable substrate; and
e. optionally, rinsing the surface of said shower.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The improved disinfecting or sanitizing substrate or pad can be used as a disinfectant, sanitizer, and/or sterilizer. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." As used herein, the term "sterilize" shall mean the complete elimination or destruction of all forms of microbial life and which is authorized under the applicable regulatory laws to make legal claims as a "Sterilant" or to have sterilizing properties or qualities.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below.

As used herein, the term "substrate" is intended to include any web which is used to clean an article or a surface. Examples of cleaning sheets include, but are not limited to, mitts, webs of material containing a single sheet of material which is used to clean a surface by hand or a sheet of material which can be attached to a cleaning implement, such as a floor mop, handle, or a hand held cleaning tool, such as a toilet cleaning device.

As used herein, "film" refers to a polymer film including flat nonporous films, and porous films such as microporous, nanoporous, closed or open celled, breathable films, or apertured films.

As used herein, "wiping" refers to any shearing action that the substrate undergoes while in contact with a target surface. This includes hand or body motion, substrate-implement motion over a surface, or any perturbation of the substrate via energy sources such as ultrasound, mechanical vibration, electromagnetism, and so forth.

As used herein, the term "fiber" includes both staple fibers, i.e., fibers which have a defined length between about 2 and about 20 mm, fibers longer than staple fiber but are not continuous, and continuous fibers, which are sometimes called "continuous filaments" or simply "filaments". The method in which the fiber is prepared will determine if the fiber is a staple fiber or a continuous filament.

As used herein, the term "nonwoven web" means a web having a structure of individual fibers or threads which are interlaid, but not in an identifiable manner as in a knitted web. Nonwoven webs have been formed from many processes, such as, for example, meltblowing processes, spunbonding processes, and bonded carded web processes. The basis weight of nonwoven webs is usually expressed in ounces of material per square yard (osy) or grams per square meter (gsm) and the fiber diameters useful are usually expressed in microns, or in the case of staple fibers, denier. It is noted that to convert from osy to gsm, multiply osy by 33.91.

The term "denier" is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. Outside the United States the unit of measurement is more commonly the "tex," which is defined as the grams per kilometer of fiber. Tex may be calculated as denier/9. The "mean fiber denier" is the sum of the deniers for each fiber, divided by the number of fibers.

As used herein, the term "bulk density" refers to the weight of a material per unit of volume and is generally expressed in units of mass per unit bulk volume (e.g., grams per cubic centimeter).

As used herein, the term "spunbonded fibers" refers to fibers which are formed by extruding molten thermoplastic material as filaments from a plurality of fine, usually circular capillaries of a spinneret with the diameter of the extruded filaments then being rapidly reduced as by, for example, U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman; U.S. Pat. No. 3,542,615 to Dobo et al.; and U.S. Pat. No. 5,382,400 to Pike et al.; the entire content of each is incorporated herein by reference. Spunbond fibers are generally not tacky when they are deposited onto a collecting surface. Spunbond fibers are generally continuous and have average diameters (from a sample of at least 10) larger than 7 microns to about 50 or 60 microns, often, between about 15 and 25 microns.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241. Meltblown fibers are microfibers, which may be continuous or discontinuous, and are generally smaller than 10 microns in average diameter, and are generally tacky when deposited onto a collecting surface.

As used herein, the term "polymer" generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, the term "conjugate fibers" refers to fibers or filaments which have been formed from at least two polymers extruded from separate extruders but spun together to form one fiber. Conjugate fibers are also sometimes referred to as "multicomponent" or "bicomponent" fibers or filaments. The term "bicomponent" means that there are two polymeric components making-up the fibers. The polymers are usually different from each other though conjugate fibers may be prepared from the same polymer, but the polymers are different from one another in some physical property, such as, for example, melting point or the softening point. The polymers are arranged in substantially constantly positioned distinct zones across the cross-section of the multicomponent fibers or filaments and extend continuously along the length of the multicomponent fibers or filaments. The configuration of such a multicomponent fiber may be, for example, a sheath/core arrangement, wherein one polymer is surrounded by another, a side-by-side arrangement, a pie arrangement or an "islands-in-the-sea" arrangement. Multicomponent fibers are taught in U.S. Pat. No. 5,108,820 to Kaneko et al., U.S. Pat. No. 5,336,552 to Strack et al., and U.S. Pat. No. 5,382,400 to Pike et al., the entire content of each is incorporated herein by reference. For two component fibers or filaments, the polymers may be present in ratios of 75/25, 50/50, 25/75 or any other desired ratios.

As used herein, the term "multiconstituent fibers" refers to fibers which have been formed from at least two polymers extruded from the same extruder as a blend or mixture. Multiconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random.

As used herein "airlaying" or "airlaid" is a well-known process by which a fibrous nonwoven layer can be formed. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air to activate a binder component or a latex adhesive. Airlaying is taught in, for example, U.S. Pat. No. 4,640,810 to Laursen et al., and U.S. Pat. No. 5,885,516 to Christensen.

As used herein, the term "hot air knife" or HAK means a process of preliminarily bonding a just produced microfiber web, particularly spunbond, in order to give it sufficient integrity, i.e. increase the stiffness of the web, for further processing, but does not mean the relatively strong bonding of secondary bonding processes like through-air bonding, thermal bonding and ultrasonic bonding. A hot air knife is a device which focuses a stream of heated air at a very high flow rate, generally from about 1000 to about 10,000 feet per minute (fpm) (305 to 3050 meters per minute), or more particularly from about 3000 to 6000 feet per minute (915 to 1830 meters per minute) directed at the nonwoven web immediately after the nonwoven web formation. The air temperature is usually in the range of the melting point of at least one of the polymers used in the web, generally between about 200° and 550° F. (93° and 290° C.) for the thermoplastic polymers commonly used in spunbonding. However, the temperature of the air must be adjusted accordingly for the particular polymers used to prepare the nonwoven web. The control of air temperature, velocity, pressure, volume and other factors helps avoid damage to the web while increasing its integrity. The HAK's focused stream of air is arranged and directed by at least one slot of about ⅛ to 1 inches (3 to 25 mm) in width, particularly about ⅜ inch (9.4 mm), serving as the exit for the heated air towards the web, with the slot running in a substantially cross-machine direction over substantially the entire width of the web. In other embodiments, there may be a plurality of slots arranged next to each other or separated by a slight gap. At least one slot is usually, though not essentially, continuous, and may be comprised of, for example, closely spaced holes. The HAK has a plenum to distribute and contain the heated air prior to its exiting the slot. The plenum pressure of the HAK is usually between about 1.0 and 12.0 inches of water (2 to 22 mmHg), and the HAK is positioned between about 0.25 and 10 inches and more preferably 0.75 to 3.0 inches (19 to 76 mm) above the forming wire. In a particular embodiment the HAK plenum's cross sectional area for cross-directional flow (i.e. the plenum cross sectional area in the machine direction) is at least twice the total slot exit area. Since the forming wire onto which spunbond polymer is formed generally moves at a high rate of speed, the time of exposure of any particular part of the web to the air discharged from the hot air knife is less a tenth of a second and generally about a hundredth of a second in contrast with the through-air bonding process which has a much larger dwell time. The HAK process has a great range of variability and controllability of many factors such as air temperature, velocity, pressure, volume, slot or hole arrangement and size, and the distance from the HAK plenum to the web. The HAK is further described in U.S. Pat. No. 5,707,468 to Arnold et al., the entire contents of which is incorporated by reference.

As used herein, through-air bonding or "TAB" means a process of bonding a nonwoven fiber web in which air, which is sufficiently hot to melt one of the polymers of which the fibers of the web are made, is forced through the web. The air velocity is between 100 and 500 feet per minute and the dwell time may be as long as 10 seconds. The melting and resolidification of the polymer provides the bonding. Through-air bonding has relatively restricted variability and since through-air bonding requires the melting of at least one component to accomplish bonding, it is generally restricted to webs with two components like multicomponent fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

As used herein "thermal point bonded" means bonding one or more fabrics with a pattern of discrete bond points. As an example, thermal point bonding often involves passing a fabric or web of fibers to be bonded at a nip between a pair of heated bonding calender rolls. One of the bonding rolls is usually, though not always, patterned in some way so that the entire fabric is not bonded across its entire surface, and the second or anvil roll is usually a smooth surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern, which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern, which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern, having generally alternating perpendicular segments, with about a 19% bond area. Typically, the percent bonding area varies from around 10% to around 30% of the area of the fabric laminate web. Point bonding may be used to hold the layers of a laminate together and/or to impart integrity to individual layers by bonding filaments and/or fibers within the web.

As used herein "pattern unbonded" or interchangeably "point unbonded" or "PUB", means a fabric pattern having continuous bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material includes providing a nonwoven fabric or web, providing opposedly positioned first and second calender rolls and defining a nip there between, with at least one of said rolls being heated and having a bonding pattern on its outermost surface comprising a continuous pattern of land areas defining a plurality of discrete openings, apertures or holes, and passing the nonwoven fabric or web within the nip formed by said rolls. Each of the openings in said roll or rolls defined by the continuous land areas forms a discrete unbonded area in at least one surface of the nonwoven fabric or web in which the fibers or filaments of the web are substantially or completely unbonded. Stated alternatively, the continuous pattern of land areas in said roll or rolls forms a continuous pattern of bonded areas that define a plurality of discrete unbonded areas on at least one surface of said nonwoven fabric or web. The PUB pattern is further described in U.S. Pat. No. 5,858,515 to Stokes et al, the entire contents of which are hereby incorporated by reference.

The term "sponge", as used herein, is meant to mean an elastic, porous material, including, but not limited to, compressed sponges, cellulosic sponges, reconstituted cellulosic sponges, cellulosic materials, foams from high internal phase emulsions, such as those disclosed in U.S. Pat. No. 6,525,106, polyethylene, polypropylene, polyvinyl alcohol, polyurethane, polyether, and polyester sponges, foams and nonwoven materials, and mixtures thereof.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic and/or amphoteric agents.

Cleaning Implement

In an embodiment of the invention, the cleaning implement comprises the tool assembly disclosed in Co-pending application Ser. No. 10/663,496, entitled "Disposable Cleaning Head", filed Sep. 12, 2003.

In another embodiment of the invention, the cleaning implement comprises the tool assembly disclosed in Co-pending application Ser. No. 10/678,033, entitled "CLEANING TOOL ASSEMBLY WITH A DISPOSABLE CLEANING IMPLEMENT", filed Sep. 30, 2003.

In an embodiment of the invention, the cleaning implement comprises the tool assembly disclosed in Co-pending application Ser. No. 10/602,478, entitled "CLEANING TOOL WITH GRIPPING ASSEMBLY FOR A DISPOSABLE SCRUBBING HEAD", filed Jun. 23, 2003.

In another embodiment of the invention, the cleaning implement comprises an elongated shaft having a handle portion on one end thereof. The tool assembly further includes a gripping mechanism that is mounted to the shaft to engage the removable cleaning pad. Examples of suitable cleaning implements are found in U.S. 2003/0070246 to Cavalheiro; U.S. Pat. No. 4,455,705 to Graham; U.S. Pat. No. 5,003,659 to Paepke; U.S. Pat. No. 6,485,212 to Bomgaars et al.; U.S. Pat. No. 6,290,781 to Brouillet, Jr.; U.S. Pat. No. 5,862,565 to Lundstedt; U.S. Pat. No. 5,419,015 to Garcia; U.S. Pat. No. 5,140,717 to Castagliola; U.S. Pat. No. 6,611,986 to Seals; U.S. 2002/0007527 to Hart; and U.S. Pat. No. 6,094,771 to Egolf et al. The cleaning implement may have a hook, hole, magnetic means, canister or other means to allow the cleaning implement to be conveniently stored when not in use.

Cleaning Pad Attachment

The cleaning implement holding the removable cleaning pad may have a cleaning head with an attachment means or the attachment means may be an integral part of the handle of the cleaning implement or may be removably attached to the end of the handle. The cleaning pad may be attached by a friction fit means, by a clamping means, by a threaded screw means, by hook and loop attachment or by any other suitable attachment means. The cleaning pad may have a rigid or flexible plastic or metal fitment for attachment to the cleaning implement or the cleaning pad may be directly attached to the cleaning implement.

Cleaning Pad Substrate

A wide variety of materials can be used as the cleaning pad substrate. The substrate should have sufficient wet strength, abrasivity, loft and porosity. Examples of suitable substrates include, nonwoven substrates, wovens substrates, hydroentangled substrates, foams and sponges.

Water-Soluble or Water-Dispersible Foam Substrate

The cleaning pad substrate may comprise a water-soluble or water-dispersible foam. The foam component may comprise a mixture of a polymeric material and a cleaning composition, the foam component being stable upon contact with air and unstable upon contact with water. The foam component may release the cleaning composition or part thereof upon contact with water, the component preferably partially or completely disintegrating, dispersing, denaturing and/or dissolving upon contact with water.

The foam and cleaning composition matrix may comprise an interconnected network of open and/or closed cells. Any polymeric material, which can be formed into a air-stable, water-unstable foam, can be used in the foam component and can be used to form the matrix or part thereof, of the foam component. The polymeric material may be a water-dispersible or a water-soluble polymer. Suitable water-dispersable polymers herein may have a dispersability of at least 50%, preferably at least 75% or even at least 95%, as measured by the method set out hereinafter using a glass-filter with a maximum pore size of 50 microns. Suitable water-soluble polymers herein may have a solubility of at least 50%, preferably at least 75% or even at least 95%, as measured by the method set out hereinafter using a glass-filter with a maximum pore size of 20 microns, namely:

Gravimetric Method for Determining Water-Solubility or Water-Dispersability of Polymers: 50 grams±0.1 gram of polymer is added in a 400 ml beaker, whereof the weight has been determined, and 245 ml±1 ml of distilled water is added. This is stirred vigorously on magnetic stirrer set at 600 rpm, for 30 minutes. Then, the water-polymer mixture is filtered through a folded qualitative sintered-glass filter with the pore sizes as defined above (max. 20 or 50 microns). The water is dried off from the collected filtrate by any conventional method, and the weight of the remaining polymer is determined (which is the dissolved or dispersed fraction). Then, the % solubility or dispersability can be calculated.

Suitable polymers are selected from cationic polymers, such as quaternary polyamines, polyvinyl alcohols, polyvinyl pyrrolidone, polyalkylene oxides, cellulose, polysaccharides, polycarboxylic acids and salts, polyaminoacids or peptides, polyamides, polyacrylamide, or derivatives or copolymers thereof. Suitable polymers are selected from polyvinyl alcohols, cellulose ethers and derivatives thereof, copolymers of maleic/acrylic acids, polysaccharides including starch and gelatine, natural gums such as xanthum and carragum. Copolymers block polymers and graft polymers of the above can also be used. Mixtures of polymers can also be used. Copolymers or mixtures of polymers may provide control of the mechanical and/or dissolution properties of the foam component, depending on the application thereof and the required needs. The polymer may have any average molecular weight from about 1000 to 1,000,000, or even from 4000 to 250,000 or even form 10,000 to 200,000 or even form 20,000 to 75,000.

Water-Soluble or Water-Dispersible Pouch

The substrate may comprise a water-soluble or water dispersible pouch or container. Suitable containers are water-soluble or water-dispersible gelatin beads, comprising cleaning compositions completely surrounded by a coating made from gelatin. The substrate may comprise a water-soluble or water-dispersible pouch. The pouch is typically a closed structure, made of a water-soluble or water-dispersible film described herein, enclosing a volume space which comprises a composition. Said composition may be in solid, gel or paste form. The pouch can be of any form, shape and material which is suitable to hold the composition, e.g., without allowing the release of the composition from the pouch prior to contact of the pouch with water. The exact execution will depend on for example, the type and amount of the composition in the pouch, the number of compartments in the pouch, the characteristics required from the pouch to hold, protect and deliver or release the composition. The pouch may be made from a water-soluble or water-dispersible film. Suitable water-soluble films are polymeric materials, preferably polymers which are formed into a film or sheet. The material in the form of a film can, for example, be obtained by casting, blow-molding, extrusion or blow extrusion of the polymer material, as known in the art. Suitable water-dispersible or water-soluble material herein has a dispersability of at least 50%, preferably at least 75% or even at least 95%, as measured by the method set out herein using a glass-filter with a maximum pore size of 50 microns.

Suitable polymers, copolymers or derivatives thereof are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. Suitable polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates. Suitable polymers are selected from polyvinyl alcohols, polyvinyl alcohol copolymers and hydroxypropyl methyl cellulose (HPMC). The polymer may have any weight average molecular weight from about 1000 to 1,000,000, or even from 10,000 to 300,000 or even from 15,000 to 200,000 or even from 20,000 to 150,000.

Also useful are polymer blend compositions, for example comprising a hydrolytically degradable and water-soluble polymer blend such as polylactide and polyvinyl alcohol, achieved by the mixing of polylactide and polyvinyl alcohol, typically comprising 1-35% by weight polylactide and approximately from 65% to 99% by weight polyvinyl alcohol, if the material is to be water-dispersible, or water-soluble.

Suitable water-soluble films are films which comprise PVA polymers and that have similar properties to the film known under the trade reference M8630, as sold by Chris-Craft Industrial Products of Gary, Ind., US. The water-soluble film herein may comprise other additive ingredients than the polymer or polymer material. For example, it may be beneficial to add plasticisers, for example glycerol, ethylene glycol, diethyleneglycol, propylene glycol, sorbitol and mixtures thereof, additional water, disintegrating aids. It may be useful that the pouch or water-soluble film itself comprises a cleaning additive.

Nonwoven Substrate

In one embodiment, the substrate of the present invention is composed of nonwoven fibers or paper. The term nonwoven is to be defined according to the commonly known definition provided by the "Nonwoven Fabrics Handbook" published by the Association of the Nonwoven Fabric Industry. A paper substrate is defined by EDANA (note 1 of ISO 9092-EN 29092) as a substrate comprising more than 50% by mass of its fibrous content is made up of fibers (excluding chemically digested vegetable fibers) with a length to diameter ratio of greater than 300, and more preferably also has density of less than 0.040 g/cm$^3$. The definitions of both nonwoven and paper substrates do not include woven fabric or cloth or sponge. The substrate can be partially or fully permeable to water. The substrate can be flexible and the substrate can be resilient, meaning that once applied external pressure has been removed the substrate regains its original shape.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The air-laying process is described in U.S. Pat. App. 2003/0036741 to Abba et al. and U.S. Pat. App. 2003/0118825 to Melius et al. The resulting layer, regardless of its method of production or composition, is then subjected to at least one of several types of bonding operations to anchor the individual fibers together to form a self-sustaining substrate. In the present invention the nonwoven substrate can be prepared by a variety of processes including, but not limited to, air-entanglement, hydroentanglement, thermal bonding, and combinations of these processes.

Additionally, the first layer and the second layer, as well as additional layers, when present, can be bonded to one another in order to maintain the integrity of the article. The layers can be heat spot bonded together or using heat generated by ultrasonic sound waves. The bonding may be arranged such that geometric shapes and patterns, e.g. diamonds, circles, squares, etc. are created on the exterior surfaces of the layers and the resulting article.

The bonding pattern can be chosen in order to maximize stiffness of the substrate. This applies in particular when bonding is effected by adhesive (chemical, such as epoxy resin adhesive, or other adhesive) or by ultrasound. Thermal or pressure bonding can be used if the layers to be bonded are appropriate for this. One preferred bonding pattern is application of adhesive or ultrasonic bonding across the full area of the substrate. Generally such patterns do not take up substantially the entire area, but generally not more than 20%, sometimes not more than 15%, but sometimes at least 5%, of the area of the substrate is covered by bonds.

One suitable application pattern for adhesive, ultrasonic or other bonds is in the form of a number of stripes extending across the width of the substrate. Preferably the stripes are parallel. The direction can be chosen depending upon the direction in which stiffness is required. For instance, if stiffness in the machine direction (this direction being defined in relation to the manufacturing process for the substrate) is required, i.e. it is required to make folding along a line extending in the transverse direction more difficult, then the stripes can extend in the machine direction. Conversely, if transverse direction stiffness is required, then stripes extending in the transverse direction can be provided. A particularly bonding pattern is one of two sets of parallel stripes at different angles, for instance in cross-hatch form. Such systems can provide the effect of introduction of a net between two layers.

The above patterns for improvement of stiffness are useful when applied to adhesive or ultrasound bonding. However, such patterns can alternatively be applied using hot melt polymer printed onto the substrate, either between layers or on an exterior surface of one of the layers. Such patterns can be applied using any low melting polymer which is flexible after application and drying and capable of producing a continuous film. Suitable polymers include polyethylene. Application of hot melt polymer can be for instance by screen or gravure printing. Screen printing is preferred. Application of hot melt polymer can be on an exterior surface on one of the layers.

Bonding can be effected after all layers intended to form the substrate have been assembled. In some embodiments, however, two or more layers can be pre-bonded prior to contacting these layers with additional layers to form the substrate.

The stiffness of the substrate when wet is an important feature. Stiffness is expressed in Taber stiffness units, preferably measured in accordance with ASTM D-5650 (resistance to bending of paper of low bending stiffness). Stiffness of the substrate when dry is measured before it is used for cleaning a surface. Stiffness of the substrate when wet is measured after it has been saturated in water. Stiffness when dry can be at least 5, or at least 8 Taber stiffness units. In particularly cases, stiffness when dry is at least 9 Taber stiffness units. The Taber stiffness when wet can be at least 5 or at least 8. In particular embodiments, the stiffness when wet can be at least 9 Taber stiffness units. Particular embodiments have stiffness when wet at least 50% or at least 60% or at least 80% or at least 90% of stiffness when dry.

The cleaning substrates can be provided dry, pre-moistened, or impregnated with cleaning composition, but dry-to-the-touch. In one aspect, dry cleaning substrates can be provided with dry or substantially dry cleaning or disinfecting agents coated on or in the multicomponent multilobal fiber layer. In addition, the cleaning substrates can be provided in a pre-moistened and/or saturated condition. The wet cleaning substrates can be maintained over time in a sealable container such as, for example, within a bucket with an attachable lid, sealable plastic pouches or bags, canisters, jars, tubs and so forth. Desirably the wet, stacked cleaning substrates are maintained in a resealable container. The use of a resealable container is particularly desirable when using volatile liquid compositions since substantial amounts of liquid can evaporate while using the first substrates thereby leaving the remaining substrates with little or no liquid. Exemplary resealable containers and dispensers include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 5,595,786 to McBride et al.; the entire contents of each of the aforesaid references are incorporated herein by reference. The cleaning substrates can be incorporated or oriented in the container as desired and/or folded as desired in order to improve ease of use or removal as is known in the art. The cleaning substrates of the present invention can be provided in a kit form, wherein a plurality of cleaning substrates and a cleaning tool are provided in a single package.

The substrate can include both natural and synthetic fibers. The substrate can also include water-soluble fibers or water-dispersible fibers, from polymers described herein. The substrate can be composed of suitable unmodified and/or modified naturally occurring fibers including cotton, Esparto grass, bagasse, hemp, flax, silk, wool, wood pulp, chemically modified wood pulp, jute, ethyl cellulose, and/or cellulose acetate. Various pulp fibers can be utilized including, but not limited to, thermomechanical pulp fibers, chemi-thermomechanical pulp fibers, chemi-mechanical pulp fibers, refiner mechanical pulp fibers, stone groundwood pulp fibers, peroxide mechanical pulp fibers and so forth.

Suitable synthetic fibers can comprise fibers of one, or more, of polyvinyl chloride, polyvinyl fluoride, polytetrafluoroethylene, polyvinylidene chloride, polyacrylics such as ORLON®, polyvinyl acetate, Rayon®, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like, including fibers comprising polymers containing more than one monomer.

The polymers suitable for the present invention include polyolefins, polyesters, polyamides, polycarbonates, polyurethanes, polyvinylchloride, polytetrafluoroethylene, polystyrene, polyethylene terephathalate, biodegradable polymers such as polylactic acid and copolymers and blends thereof. Suitable polyolefins include polyethylene, e.g., high density polyethylene, medium density polyethylene, low density polyethylene and linear low density polyethylene; polypropylene, e.g., isotactic polypropylene, syndiotactic polypropylene, blends of isotactic polypropylene and atactic polypropylene, and blends thereof, polybutylene, e.g., poly (1-butene) and poly(2-butene); polypentene, e.g., poly(1-pentene) and poly(2-pentene); poly(3-methyl-1-pentene); poly(4-methyl 1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include polyethylene terephthalate, polytrimethylene terephthalate, polybutylene terephthalate, polytetramethylene terephthalate, polycyclohexylene-1, 4-dimethylene terephthalate, and isophthalate copolymers thereof, as well as blends thereof.

Many polyolefins are available for fiber production, for example polyethylenes such as Dow Chemical's ASPUN 6811A linear low-density polyethylene, 2553 LLDPE and 25355 and 12350 high density polyethylene are such suitable polymers. The polyethylenes have melt flow rates in g/10 min. at 190° F. and a load of 2.16 kg, of about 26, 40, 25 and 12, respectively. Fiber forming polypropylenes include Exxon Chemical Company's ESCORENE PD3445 polypropylene. Many other polyolefins are commercially available and generally can be used in the present invention. The particularly preferred polyolefins are polypropylene and polyethylene.

Examples of polyamides and their methods of synthesis may be found in "Polymer Resins" by Don E. Floyd (Library of Congress Catalog number 66-20811, Reinhold Publishing, N.Y., 1966). Particularly commercially useful polyamides are nylon 6, nylon-6,6, nylon-11 and nylon-12. These polyamides are available from a number of sources such as Custom Resins, Nyltech, among others. In addition, a compatible tackifying resin may be added to the extrudable compositions described above to provide tackified materials that autogenously bond or which require heat for bonding. Any tackifier resin can be used which is compatible with the polymers and can withstand the high processing (e.g., extrusion) temperatures. If the polymer is blended with processing aids such as, for example, polyolefins or extending oils, the tackifier resin should also be compatible with those processing aids. Generally, hydrogenated hydrocarbon resins are preferred tackifying resins, because of their better temperature stability. REGALREZ® and ARKON® P series tackifiers are examples of hydrogenated hydrocarbon resins. ZONATAC® 501 lite is an example of a terpene hydrocarbon. REGALREZ® hydrocarbon resins are available from Hercules Incorporated. ARKON® series resins are available from Arakawa Chemical (USA) Incorporated. The tackifying resins such as disclosed in U.S. Pat. No. 4,787,699, hereby incorporated by reference, are suitable. Other tackifying resins which are compatible with the other components of the composition and can withstand the high processing temperatures, can also be used.

It is desirable that the particular polymers used for the different components of the fibers in the practice of the invention have melting points different from one another. This is important not only in producing crimped fibers but also when through-air bonding is used as the bonding technique, wherein the lower melting polymer bonds the fibers together to form the fabric or web. It is desirable that the lower melting point polymers makes up at least a portion of the outer region of the fibers. More particularly, the lower melting component should be located in an outer portion of the fiber so that it comes in contact with other fibers. For example, in a sheath/core fiber configuration, the lower melting point polymer component should be located in the sheath portion. In a side-by-side configuration, the lower melting point polymer will inherently be located on an outer portion of the fiber.

The proportion of higher and lower melting polymers in the multicomponent, multilobal fibers can range between about 10-90% by weight higher melting polymer and 10-90% lower melting polymer. In practice, only so much lower melting polymer is needed as will facilitate bonding between the fibers. Thus, a suitable fiber composition may contain about 40-80% by weight higher melting polymer and about 20-60% by weight lower melting polymer, desirably about 50-75% by weight higher melting polymer and about 25-50% by weight lower melting polymer. In one embodiment, a first polymer, which is the lower melting point polymer is polyethylene and the higher melting point polymer is polypropylene.

The cleaning substrate of this invention may be a multi-layer laminate and may be formed by a number of different techniques including but not limited to using adhesive, needle punching, ultrasonic bonding, thermal calendering and through-air bonding. Such a multilayer laminate may be an embodiment wherein some of the layers are spunbond and some meltblown such as a spunbond/meltblown/spunbond (SMS) laminate as disclosed in U.S. Pat. No. 4,041,203 to Brock et al. and U.S. Pat. No. 5,169,706 to Collier, et al., each hereby incorporated by reference. The SMS laminate may be made by sequentially depositing onto a moving conveyor belt or forming wire first a spunbond web layer, then a meltblown web layer and last another spunbond layer and then bonding the laminate in a manner described above. Alternatively, the three web layers may be made individually, collected in rolls and combined in a separate bonding step.

The substrate can comprise solely naturally occurring fibers, solely synthetic fibers, or any compatible combination of naturally occurring and synthetic fibers.

The fibers useful herein can be hydrophilic, hydrophobic or can be a combination of both hydrophilic and hydrophobic fibers. As indicated above, the particular selection of hydrophilic or hydrophobic fibers depends upon the other materials included in the absorbent (and to some degree) the scrubbing layer described hereinafter. Suitable hydrophilic fibers for use in the present invention include cellulosic fibers, modified cellulosic fibers, rayon, cotton, and polyester fibers, such as hydrophilic nylon (HYDROFIL®). Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like.

Another type of hydrophilic fiber for use in the present invention is chemically stiffened cellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Where fibers are used as the absorbent layer (or a constituent component thereof), the fibers can optionally be combined with a thermoplastic material. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers. This can be beneficial in providing additional overall integrity to the cleaning substrate.

Amongst its various effects, bonding at the fiber intersections increases the overall compressive modulus and strength of the resulting thermally bonded member. In the case of the chemically stiffened cellulosic fibers, the melting and migration of the thermoplastic material also has the effect of increasing the average pore size of the resultant web, while maintaining the density and basis weight of the web as originally formed. This can improve the fluid acquisition properties of the thermally bonded web upon initial exposure to fluid, due to improved fluid permeability, and upon subsequent exposure, due to the combined ability of the stiffened fibers to retain their stiffness upon wetting and the ability of the thermoplastic material to remain bonded at the fiber intersections upon wetting and upon wet compression. In net, thermally bonded webs of stiffened fibers retain their original overall volume, but with the volumetric regions previously occupied by the thermoplastic material becoming open to thus increase the average interfiber capillary pore size.

Thermoplastic materials useful in the present invention can be in any of a variety of forms including particulates, fibers, or combinations of particulates and fibers. Thermoplastic fibers are a particularly preferred form because of their ability to form numerous interfiber bond sites. Suitable thermoplastic materials can be made from any thermoplastic polymer that can be melted at temperatures that will not extensively damage the fibers that comprise the primary web or matrix of each layer. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in the cleaning pads, are likely to be stored. The melting point of the thermoplastic material is typically no lower than about 50° C.

The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g per square centimeter of thermoplastic fiber.

Suitable thermoplastic fibers can be made from a single polymer (monocomponent fibers), or can be made from more than one polymer (e.g., bicomponent or multicomponent fibers). Multicomponent fibers are described in U.S. Pat. App. 2003/0106568 to Keck and Arnold. Bicomponent fibers are described in U.S. Pat. No. 6,613,704 to Arnold and Myers and references therein. Multicomponent fibers of a wide range of denier or dtex are described in U.S. Pat. App. 2002/0106478 to Hayase et. al. The "bicomponent fibers" may be thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., those available from Danaklon a/s, Chisso Corp., and CELBOND®, available from Hercules). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses.

Methods for preparing thermally bonded fibrous materials are described in U.S. Pat. No. 5,607,414 to Richards et al. and U.S. Pat. No. 5,549,589 to Homey et al. The absorbent layer can also comprise a HIPE-derived hydrophilic, polymeric foam. Such foams and methods for their preparation are described in U.S. Pat. No. 5,550,167 to DesMarais and U.S. Pat. No. 5,563,179 to Stone et al. The disclosures of these references are incorporated by reference herein.

Various forming methods can be used to form a suitable fibrous web. For instance, the web can be made by nonwoven dry forming techniques, such as air-laying, or alternatively by wet laying, such as on a paper making machine. Other nonwoven manufacturing techniques, including but not limited to techniques such as melt blown, spunbonded, needle punched, and hydroentanglement methods can also be used. In one embodiment, the dry fibrous web can be an airlaid nonwoven web comprising a combination of natural fibers, staple length synthetic fibers and a latex binder. The dry fibrous web can be about 20-80 percent by weight wood pulp fibers, 10-60 percent by weight staple length polyester fibers, and about 10-25 percent by weight binder.

The dry, fibrous web can have a basis weight of between about 30 and about 200 grams per square meter. The density of the dry web can be measured after evaporating the liquid from the premoistened wipe, and the density can be less than about 0.15 grams per cubic centimeter. The bulk density is the basis weight of the dry web divided by the thickness of the dry web, measured in consistent units, and the thickness of the dry web is measured using a circular load foot having an area of about 2 square inches and which provides a confining pressure of about 95 grams per square inch. In one embodiment, the dry web can have a basis weight of about 64 grams per square meter, a thickness of about 0.06 cm, and a bulk density of about 0.11 grams per cubic centimeter.

The following patents are incorporated herein by reference for their disclosure related to webs: U.S. Pat. Nos. 3,862,472; 3,982,302; 4,004,323; 4,057,669; 4,097,965; 4,176,427; 4,130,915; 4,135,024; 4,189,896; 4,207,367; 4,296,161; 4,309,469; 4,682,942; 4,637,859; 5,223,096; 5,240,562; 5,556,509; and 5,580,423.

In one embodiment, the cleaning substrate has at least two regions where the regions are distinguished by basis weight. Briefly, the measurement is achieved photographically, by differentiating dark (low basis weight) and light (high basis) network regions. In particular, the cleaning substrate comprises one or more low basis weight regions, wherein the low basis region(s) have a basis weight that is not more than about 80% of the basis weight of the high basis weight regions. In one aspect, the first region is relatively high basis weight and comprises an essentially continuous network. The second region comprises a plurality of mutually discrete regions of relatively low basis weight and which are circumscribed by the high basis weight first region. In particular, a cleaning substrate may comprise a continuous region having a basis weight of from about 30 to about 120 grams per square meter and a plurality of discontinuous regions circumscribed by the high basis weight region, wherein the discontinuous regions are disposed in a random, repeating pattern and having a basis weight of not more than about 80% of the basis weight of the continuous region.

In one embodiment, the cleaning substrate will have, in addition to regions which differ with regard to basis weight, substantial macroscopic three-dimensionality. The term "macroscopic three-dimensionality", when used to describe three dimensional cleaning substrates means a three-dimensional pattern is readily visible to the naked eye when the perpendicular distance between the viewer's eye and the plane of the substrate is about 12 inches. In other words, the three dimensional structures of the pre-moistened substrates of the present invention are cleaning substrates that are non-planar, in that one or both surfaces of the substrates exist in multiple planes. By way of contrast, the term "planar", refers to substrates having fine-scale surface aberrations on one or both sides, the surface aberrations not being readily visible to the naked eye when the perpendicular distance between the viewer's eye and the plane of the sheet is about 12 inches. In other words, on a macro scale the observer will not observe that one or both surfaces of the substrate will exist in multiple planes so as to be three-dimensional.

Briefly, macroscopic three-dimensionality is described in terms of average height differential, which is defined as the average distance between adjacent peaks and valleys of a given surface of a substrate, as well as the average peak to peak distance, which is the average distance between adjacent peaks of a given surface. Macroscopic three dimensionality is also described in terms of surface topography index of the outward surface of a cleaning substrate; surface topography index is the ratio obtained by dividing the average height differential of a surface by the average peak to peak distance of that surface. In one embodiment, a macroscopically three-dimensional cleaning substrate has a first outward surface and a second outward surface wherein at least one of the outward surfaces has a peak to peak distance of at least about 1 mm and a surface topography index from about 0.01 mm to about 10 mm. The macroscopically three-dimensional structures of the substrates of the present invention optionally comprise a scrim, which when heated and the cooled, contract so as to provide further macroscopic three-dimensional structure.

In another embodiment, the substrate can comprise a laminate of two outer hydroentangled webs, such as nonwoven webs of polyester, rayon fibers or blends thereof having a basis weight of about 10 to about 60 grams per square meter, joined to an inner constraining layer, which can be in the form of net like scrim material which contracts upon heating to provide surface texture in the outer layers.

The pre-moistened substrate can be made by wetting the dry substrate with at least about 1.0 gram of liquid composition per gram of dry fibrous web. The dry substrate can be wetted with at least about 1.5 or at least about 2.0 grams of liquid composition per gram of the dry fibrous web. The exact amount of solution impregnated on the substrate will depend on the product's intended use. For pre-moistened substrates intended to be used for cleaning counter tops, stove tops, glass etc., optimum wetness is from about 1 gram of solution to about 5 grams of solution per gram of substrate. In the context of a floor-cleaning substrate, the pre-moistened substrate can preferably include an absorbent core reservoir with a large capacity to absorb and retain fluid. The absorbent reservoir can have a fluid capacity of from about 5 grams to about 15 grams per gram of absorptive material. Pre-moistened substrates intended to be used for the cleaning of walls, exterior surfaces, etc. will have a capacity of from about 2 grams to about 10 grams of dry fibrous web.

In addition to having substrates prepared using a monolayer substrate, it is advantageous in some situations to have the substrate constructed having multiple layers. In one embodiment, the substrate consists of a multi-laminate structure comprising a pre-moistened outer layer, an impermeable film or membrane inner layer and second outer-layer which is substantially dry. To improve the wet capacity of the substrate and to protect the back layer from getting prematurely wet, an optional absorbent reservoir can be placed between the pre-moistened first outer-layer and the impermeable film or membrane. The dimensions of the reservoir can be smaller than the dimensions of the two outer layers to prevent liquid wicking from the front layer onto the back layer.

When a multi-laminate structure is used, the outer layer can contain at least about 30% hydrophobic fibers. The impermeable inner layer can be polyethylene, polypropylene or mixtures thereof. The composition mixture and thickness of the impermeable layer can be chosen so as to minimize any seepage of liquid from the pre-moistened first outer-layer to the dry second outer-layer. Those skilled in the art will appreciate that use of a reservoir core or of a high fluid capacity outer-layer will test the impermeable layer, such that more than one impermeable layer can be required to ensure sufficient dryness for the second outer-layer of the substrate. The reservoir, if present, can consist of treated or untreated cellulose, either as a stand alone material or as a hybrid with hydrophobic fibers. The hydrophobic content of the reservoir layer can be less than about 30% or less than about 20% by weight of the total fiber content of the layer. In one embodiment, the reservoir consists of air-laid cellulose. The second outer-layer, which is substantially dry-to-the-touch, can consist of high absorbency cellulose or blends of cellulose and synthetic fibers.

Chemical bonding utilizes a solvent or adhesive, and U.S. Pat. No. 3,575,749 to Kroyer discloses bonding the fibrous layer with a latex binder, which may be applied to one or both sides of the web. Binders may comprise liquid emulsions, latex binders, liquid adhesives, chemical bonding agents, and mixtures thereof. The binder composition can be made using a latex adhesive commercially available as Rovene 5550 (49 percent solids styrene butadiene) available from Mallard Creek Polymers of Charlotte, N.C. Other suitable binders are available from National Starch and Chemical, including DUR-O-SET 25-149A (Tg=+9° C.), NACRYLIC 25-012A (Tg=−34° C.), NACRYLIC 25-4401 (Tg=−23° C.), NACRYLIC ABX-30-25331A, RESYN 1072 (Tg=+37° C.), RESYN 1601, X-LINK 25-033A, DUR-O-SET C310, DUR-O-SET ELITE ULTRA, (vinylacetate hompolymers and copolymers), STRUCTURECOTE 1887 (modified starch), NATIONAL 77-1864 (Tg=+100° C.)(modified starch), TYLAC NW-4036-51-9 (styrene-butadiene terpolymer), and from Air Products Polymers, including Flexbond AN214 (Tg=+30° C.)(vinylacetate copolymer). A latex emulsion or solution, typically in an aqueous medium, is applied to one or both surfaces of the web to provide a latex coating which partially impregnates the web, and upon curing stabilizes the structure. The latex may be applied to the web by any suitable means such as spraying, brushing, flooding, rolling, and the like. The amount of latex applied and the degree of penetration of the latex are controlled so as to avoid impairing the effective absorbency.

The substrate may also contain superabsorbent materials. A wide variety of high absorbency materials (also known as superabsorbent materials) are known to those skilled in the art. See, for example, U.S. Pat. No. 4,076,663 issued Feb. 28, 1978 to Masuda et al, U.S. Pat. No. 4,286,082 issued Aug. 25, 1981 to Tsubakimoto et al., U.S. Pat. No. 4,062,817 issued Dec. 13, 1977 to Westerman, and U.S. Pat. No. 4,340,706 issued Jul. 20, 1982 to Obayashi et al. The absorbent capacity of such high-absorbency materials is generally many times greater than the absorbent capacity of fibrous materials. For example, a fibrous matrix of wood pulp fluff can absorb about 7-9 grams of a liquid, (such as 0.9 weight percent saline) per gram of wood pulp fluff, while the high-absorbency materials can absorb at least about 15, preferably at least about 20, and often at least about 25 grams of liquid, such as 0.9 weight percent saline, per gram of the high-absorbency material. U.S. Pat. No. 5,601,542, issued to Melius et al., discloses an absorbent article in which superabsorbent material is contained in layers of discrete pouches. Alternately, the superabsorbent material may be within one layer or dispersed throughout the substrate.

The superabsorbent materials can be natural, synthetic, and modified natural polymers and materials. In addition, the superabsorbent materials can be inorganic materials, such as silica gel, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations of Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbents may be particulate or fibrous, and are preferably particulate. Superabsorbents are generally available in particle sizes ranging from about 20 to about 1000 microns. Preferred particle sizes range from 100 to 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® 880 available from Stockhausen, located in Sweden. FAVOR® 880 is presently preferred because of its high gel strength. An example of a fibrous superabsorbent is OASIS® 101, available from Technical Absorbents, located in Grimsby, United Kingdom.

The cleaning substrate, upon which the cleaning composition is loaded thereon, is made of an absorbent/adsorbent material. Typically, the cleaning substrate has at least one layer of nonwoven material. The loading ratio of the cleaning composition onto the cleaning substrate is about 2-5:1, and typically about 3-4:1. The cleaning composition is loaded onto the cleaning substrate in any number of manufacturing methods.

Examples of suitable nonwoven water insoluble substrates include, 100% cellulose Wadding Grade 1804 from Little Rapids Corporation, 100% polypropylene needlepunch material NB 701-2.8-W/R from American Non-wovens Corporation, a blend of cellulosic and synthetic fibres-Hydraspun 8579 from Ahlstrom Fibre Composites, and &0% Viscose/30% PES Code 9881 from PGI Nonwovens Polymer Corp. Another useful substrate is manufactured by Jacob Holm-Lidro Rough. It is a composition material comprising a 65/35 viscose rayon/polyester hydroentangled spunlace layer with a hydroenlongated bonded polyeser scribbly layer. Still another useful substrate is manufactured by Texel "TI". It is a composite material manufactured from a layer of coarse fiber 100% polypropylene needlepunch, an absorbent cellulose core and a fine fiber polyester layer needlepunched together. The polypropylene layer can range from 1.5 to 3.5 oz/sq. yd. The cellulose core is a creped paper layer ranging from 0.5 to 2 oz./sq. yd. The fine fiber polyester layer can range from 0.5 to 2 oz./sq. yd. Still another composite material manufactured by Texcel from a layer of coarse fiber 100% polypropylene needlepunch layer, an absorbent cellulose core and a fine fiber polyester layer needlepunched together. The polypropylene layer can range from 1.5 to 3.5 oz/sq. yd. The cellulose core is a creped paper layer ranging from 0.5 to 2 oz/sq. yd. The fine fiber polyester layer can range from 0.5 to 2 oz/sq. yd. The polypropylene layer is flame treated to further increase the level of abrasivity. The temperature of the flame and the length of time the material is exposed can be varied to create different levels of surface roughness.

Ahlstrom manufactures a hydroentangled nonwoven created from a blend of cellulosic and polyester and/or polypropylene fibers with an abrasive side. The basis weight can range from 1.2 to 6 ounces per square yard.

A composite dual textured material manufactured by Kimberly Clark comprises a coarse meltblown polypropylene, polyethylene, or polyester and high loft spunbond polyester. The two materials can be laminated together using chemical adhesives or by coprocessing the two layers. The coarse meltblown layer can range from 1 to 3 ounces per square yard while the highloft spunbond layer can range from 1 to 3 ounces per square yard.

Another example of a composite is a dual textured material composed of coarse meltblown polypropylene, polyethylene, or polyester and polyester/cellulose coform. The two materials can be laminated together using chemical adhesives or by coprocessing the two layers. The coarse meltblown layer can range from 1 to 3 ounces per square yard. The coform layer can range in composition from 30% cellulose and 70% polyester to 70% cellulose and 30% polyester and the basis weight can range from 1.5 to 4.5 ounces per square yard.

The product of the present invention comprising multiple layers may be ultrasonically bonded after applying the coating of one or more of the layers. Alternatively, layers may be bonded together by needlepunch, thermal bonding, chemical bonding, or sonic bonding prior to applying the coating and/or impregnation.

Tensile Strength

A sufficient seal strength between laminated layers is important to prevent the layers from peeling off one another. The seal strength is measured by a tensile tester. The tensile tester is a device constructed in such a way that a gradually increasing load is smoothly applied to a defined sample portion until the sample portion breaks. The tensile at the point of breakage (at which time the sample breaks) is frequently called "peak" tensile, or just "peak". The suitable instrument used for the measurement is Instron 5564 which may be equipped with either digital readout or strip chart data display for load and elongation. The following procedure is conducted under standard laboratory conditions at 23° C. (73° F.) and 50% relative humidity for a minimum of 2.0 hours. (1) Cut a sample into a strip having 1 inch by 5 inches size. At least three strips should be prepared for the measurement. (2) Put the sample strip in the instrument. The way to set the sample strip is to insert the sample strip into the top clamp of the instrument first, and then to clamp the sample strip into the bottom clamp with enough tension to eliminate any slack of the sample strip. (3) Strain the sample strip at 5 inches/minute until breaking it. (4) Read the peak tensile value. (5) Repeat the above procedures (1) to (4) for the other sample strips. (6) Calculate the average tensile as follows: Average Tensile (g/in)=Sum of the peak loads for samples tested divided by the number of test strips tested The average tensile value for use herein is the average tensile of the three samples. Calculate and report to the nearest whole unit. The seal strength may be at least 120 g/in, preferably 300 g/in, and more preferably 500 g/in to prevent tearing during use.

Cleaning Composition

In one embodiment, the cleaning device comprises a cleaning substrate that is impregnated with a cleaning composition and is 'wet-to-the-touch'. In another embodiment, the cleaning device comprises a cleaning substrate that is impregnated with a cleaning composition that is 'dry-to-the-touch'. By 'dry-to-the-touch', it is meant that the substrate has no visible liquid on the outside of the substrate and does not drip under gravity, but without externally applied pressure. A 'dry-to-the-touch' substrate may expell liquid when squeezed. In another embodiment, the cleaning device contains a removable attached vessel containing a cleaning composition and the cleaning substrate is free of the cleaning composition.

The cleaning composition may contain one or more surfactants selected from anionic, nonionic, cationic, ampholytic, amphoteric and zwitterionic surfactants and mixtures thereof. A typical listing of anionic, nonionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. Where present, ampholytic, amphotenic and zwitterionic surfactants are generally used in combination with one or more anionic and/or nonionic surfactants. The surfactants may be present at a level of from about 0% to 90%, or from about 0.001% to 50%, or from about 0.01% to 25% by weight.

The cleaning composition may comprise an anionic surfactant. Essentially any anionic surfactants useful for detersive purposes can be comprised in the cleaning composition. These can include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyl-diphenyloxide disulfonate, as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated C12-C18 monoesters) diesters of sulfosuccinate (for instance saturated and unsaturated C6-C14 diesters), N-acyl sarcosinates. Resin acids and hydrogenated resin acids are also suitable, such as rosin, hydrogenated rosin, and resin acids and hydrogenated resin acids present in or derived from tallow oil. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the C5-C17acyl-N—(C1-C4 alkyl) and —N—(C1-C2 hydroxyalkyl)glucamine sulfates, and sulfates of alkylpolysaccharides such as the sulfates of alkylpolyglucoside (the nonionic nonsulfated compounds being described herein). Alkyl sulfate surfactants may be selected from the linear and branched primary C10-C18 alkyl sulfates, the C11-C15 branched chain alkyl sulfates, or the C12-C14 linear chain alkyl sulfates.

Alkyl ethoxysulfate surfactants may be selected from the group consisting of the C10-C18 alkyl sulfates which have been ethoxylated with from 0.5 to 20 moles of ethylene oxide per molecule. The alkyl ethoxysulfate surfactant may be a C11-C18, or a C11-C15 alkyl sulfate which has been ethoxylated with from 0.5 to 7, or from 1 to 5, moles of ethylene oxide per molecule. One aspect of the invention employs mixtures of the alkyl sulfate and/or sulfonate and alkyl ethoxysulfate surfactants. Such mixtures have been disclosed in PCT Patent Application No. WO 93/18124.

Anionic sulfonate surfactants suitable for use herein include the salts of C5-C20 linear alkylbenzene sulfonates, alkyl ester sulfonates, C6-C22 primary or secondary alkane sulfonates, C6-C24 olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylates, the alkyl polyethoxy polycarboxylate surfactants and the soaps ('alkyl carboxyls'), especially certain secondary soaps as described herein. Suitable alkyl ethoxy carboxylates include those with the formula $RO(CH_2CH_2O)_xCH_2COO^-M^+$ wherein R is a C6 to C18 alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula $RO-(CHR^1-CHR^2-O)-R^3$ wherein R is a C6 to C18 alkyl group, x is from 1 to 25, $R^1$ and $R^2$ are selected from the group consisting of hydrogen, methyl acid radical, succinic acid radical, hydroxysuccinic acid radical, and mixtures thereof, and $R^3$ is selected from the group consisting of hydrogen, substituted or unsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula $R-CON(R^1)CH-)COOM$, wherein R is a C5-C17 linear or branched alkyl or alkenyl group, $R^1$ is a C1-C4 alkyl group and M is an alkali metal ion. Examples are the myristyl and oleoyl methyl sarcosinates in the form of their sodium salts.

Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein are those having the structural formula $R^2CONR^1Z$ wherein: $R^1$ is H, C1-C4 hydrocarbyl, 2-hydroxyethyl, 2-hydroxypropyl, ethoxy, propoxy, or a mixture thereof, for instance, C1-C4 alkyl, or C1 or C2 alkyl; and $R^2$ is a C5-C31 hydrocarbyl, for instance, straight-chain C5-C19 alkyl or alkenyl, or straight-chain C9-C17 alkyl or alkenyl, or straight-chain C11-C17 alkyl or alkenyl, or mixture thereof-, and Z is a polyhydroxyhydrocarbyl having a linear hydrocarbyl chain with at least 3 hydroxyls directly connected to the chain, or an alkoxylated derivative (for example, ethoxylated or propoxylated) thereof. Z may be derived from a reducing sugar in a reductive amination reaction, for example, Z is a glycityl.

Suitable fatty acid amide surfactants include those having the formula: $R^1CON(R^2)_2$ wherein $R^1$ is an alkyl group containing from 7 to 21, or from 9 to 17 carbon atoms and each $R^2$ is selected from the group consisting of hydrogen, C1-C4 alkyl, C1-C4 hydroxyalkyl, and $-(C_2H_4O)_xH$, where x is in the range of from 1 to 3.

Suitable alkylpolysaccharides for use herein are disclosed in U.S. Pat. No. 4,565,647 to Llenado, having a hydrophobic group containing from 6 to 30 carbon atoms and a polysaccharide, e.g., a polyglycoside, hydrophilic group containing from 1.3 to 10 saccharide units. Alkylpolyglycosides may have the formula: $R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl may be derived from glucose.

Suitable amphoteric surfactants for use herein include the amine oxide surfactants and the alkyl amphocarboxylic acids. Suitable amine oxides include those compounds having the formula $R^3(OR^4)_xNO(R^5)_2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof, x is from 0 to 5, preferably from 0 to 3; and each $R^5$ is an alkyl or hydroxyalkyl group containing from 1 to 3, or a polyethylene oxide group containing from 1 to 3 ethylene oxide groups. Suitable amine oxides are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Zwitterionic surfactants can also be incorporated into the cleaning compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are exemplary zwitterionic surfactants for use herein.

Suitable betaines are those compounds having the formula $R(R^1)_2N^+R^2COO^-$ wherein R is a C6-C18 hydrocarbyl. group, each $R^1$ is typically C1-C3 alkyl, and $R^2$ is a C1-C5 hydrocarbyl group. Suitable betaines are C12-18 dimethylammonio hexanoate and the C10-18 acylamidopropane (or ethane) dimethyl (or diethyl) betaines. Complex betaine surfactants are also suitable for use herein.

Suitable cationic surfactants to be used herein include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants.

Another suitable group of cationic surfactants, which can be used in the cleaning compositions, are cationic ester surfactants. The cationic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting, of carbon, nitrogen and oxygen atoms and any mixtures thereof, with the proviso that any nitrogen or oxygen atom in said chain connects only with carbon atoms in the chain. Thus spacer groups having, for example, —O—O— (i.e. peroxide), —N—N—, and —N—O— linkages are excluded, whilst spacer groups having, for example —CH$^2$—O—, CH$_2$— and —CH$_2$—NH—CH$_2$— linkages are included. The spacer group chain may comprise only carbon atoms, or the chain is a hydrocarbyl chain.

The cleaning composition may comprise cationic monoalkoxylated amine surfactants, for instance, of the general formula: $R^1R^2R^3N^+ApR^4X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for instance, methyl, for instance, both $R^2$ and $R^3$ are methyl groups; $R^4$ is selected from hydrogen, methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $ApR^4$ group in the formula may have p=1 and is a hydroxyalkyl group, having no greater than 6 carbon atoms whereby the —OH group is separated from the quaternary ammonium nitrogen atom by no more than 3 carbon atoms. Suitable $ApR^4$ groups are —CH$_2$CH$_2$—OH, —CH$_2$CH$_2$CH$_2$—OH, —CH$_2$CH(CH$_3$)—OH and —CH(CH$_3$)CH$_2$—OH. Suitable $R^1$ groups are linear alkyl groups, for instance, linear $R^1$ groups having from 8 to 14 carbon atoms.

Suitable cationic mono-alkoxylated amine surfactants for use herein are of the formula $R^1(CH_3)(CH_3)N^+(CH_2CH_2O)_{2-5}HX^-$ wherein $R^1$ is C10-C18 hydrocarbyl and mixtures thereof, especially C10-C14 alkyl, or C10 and C12 alkyl, and X is any convenient anion to provide charge balance, for instance, chloride or bromide.

As noted, compounds of the foregoing type include those wherein the ethoxy (CH$_2$CH$_2$O) units (EO) are replaced by butoxy, isopropoxy [CH(CH$_3$)CH$_2$O] and [CH$_2$CH(CH$_3$)O] units (i-Pr) or n-propoxy units (Pr), or mixtures of EO and/or Pr and/or i-Pr units.

The cationic bis-alkoxylated amine surfactant may have the general formula: $R^1R^2N^+ApR^3A'qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is an anion such as chloride, bromide, methylsulfate, sulfate, or the like, sufficient to provide electrical neutrality. A and A' can vary independently and are each selected from C1-C4 alkoxy, for instance, ethoxy, (i.e., —CH$_2$CH$_2$O—), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein are of the formula $R^1CH_3N^+(CH_2CH_2OH)(CH_2CH_2OH)X^-$, wherein $R^1$ is C10-C18 hydrocarbyl and mixtures thereof, or C10, C12, C14 alkyl and mixtures thereof, $X^-$ is any convenient anion to provide charge balance, for example, chloride. With reference to the general cationic bis-alkoxylated amine structure noted above, since in one example compound $R^1$ is derived from (coconut) C12-C14 alkyl fraction fatty acids, $R^2$ is methyl and $ApR^3$ and $A'qR^4$ are each monoethoxy.

Other cationic bis-alkoxylated amine surfactants useful herein include compounds of the formula: $R^1R^2N^+—(CH_2CH_2O)_pH—(CH_2CH_2O)_qH X^-$ wherein $R^1$ is C10-C18 hydrocarbyl, or C10-C14 alkyl, independently p is 1 to about 3 and q is 1 to about 3, $R^2$ is C1-C3 alkyl, for example, methyl, and $X^-$ is an anion, for example, chloride or bromide.

Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3)O$] units (i-Pr) or n-propoxy units (Pr), or mixtures of EO and/or Pr and/or i-Pr units.

The inventive compositions may include at least one fluorosurfactant selected from nonionic fluorosurfactants, cationic fluorosurfactants, and mixtures thereof which are soluble or dispersible in the aqueous compositions being taught herein, sometimes compositions which do not include further detersive surfactants, or further organic solvents, or both. Suitable nonionic fluorosurfactant compounds are found among the materials presently commercially marketed under the tradename Fluorad® (ex. 3M Corp.) Exemplary fluorosurfactants include those sold as Fluorad® FC-740, generally described to be fluorinated alkyl esters; Fluorad® FC-430, generally described to be fluorinated alkyl esters; Fluorad® FC-431, generally described to be fluorinated alkyl esters; and, Fluorad® FC-170-C, which is generally described as being fluorinated alkyl polyoxyethlene ethanols.

Suitable nonionic fluorosurfactant compounds include those which is believed to conform to the following formulation: $C_nF_{2n+1}SO_2N(C_2H_5)(CH_2CH_2O)_xCH_3$ wherein: n has a value of from 1-12, or from 4-12, or 8; x has a value of from 4-18, or from 4-10, or 7; which is described to be a nonionic fluorinated alkyl alkoxylate and which is sold as Fluorad® FC-171 (ex. 3M Corp., formerly Minnesota Mining and Manufacturing Co.).

Additionally suitable nonionic fluorosurfactant compounds are also found among the materials marketed under the tradename ZONYL® (DuPont Performance Chemicals). These include, for example, ZONYL® FSO and ZONYL® FSN. These compounds have the following formula: $RfCH_2CH_2O(CH_2CH_2O)_xH$ where Rf is $F(CF_2CF_2)_y$. For ZONYL® FSO, x is 0 to about 15 and y is 1 to about 7. For ZONYL® FSN, x is 0 to about 25 and y is 1 to about 9.

An example of a suitable cationic fluorosurfactant compound has the following structure: $C_nF_{2n+1}SO_2NHC_3H_6N^+(CH_3)_3I^-$ where n~8. This cationic fluorosurfactant is available under the tradename Fluorad® FC-135 from 3M. Another 0example of a suitable cationic fluorosurfactant is $F^3$—$(CF_2)_n$—$(CH_2)_m SCH_2CHOH$—$CH_2$—$N^+$ $R_1R_2R_3Cl^-$ wherein: n is 5-9 and m is 2, and $R_1$, $R_2$ and $R_3$ are —$CH_3$. This cationic fluorosurfactant is available under the tradename ZONYL® FSD (available from DuPont, described as 2-hydroxy-3-((gamma-omega-perfluoro-$C_{6-20}$-alkyl)thio)-N,N,N-trimethyl-1-propyl ammonium chloride). Other cationic fluorosurfactants suitable for use in the present invention are also described in EP 866,115 to Leach and Niwata.

The fluorosurfactant selected from the group of nonionic fluorosurfactant, cationic fluorosurfactant, and mixtures thereof may be present in amounts of from 0.001 to 5% wt., preferably from 0.01 to 1% wt., and more preferably from 0.01 to 0.5% wt.

Solvent

Suitable organic solvents include, but are not limited to, $C_{1-6}$ alkanols, $C_{1-6}$ diols, $C_{1-10}$ alkyl ethers of alkylene glycols, $C_{3-24}$ alkylene glycol ethers, polyalkylene glycols, short chain carboxylic acids, short chain esters, isoparafinic hydrocarbons, mineral spirits, alkylaromatics, terpenes, terpene derivatives, terpenoids, terpenoid derivatives, formaldehyde, and pyrrolidones. Alkanols include, but are not limited to, methanol, ethanol, n-propanol, isopropanol, butanol, pentanol, and hexanol, and isomers thereof. Diols include, but are not limited to, methylene, ethylene, propylene and butylene glycols. Alkylene glycol ethers include, but are not limited to, ethylene glycol monopropyl ether, ethylene glycol monobutyl ether, ethylene glycol monohexyl ether, diethylene glycol monopropyl ether, diethylene glycol monobutyl ether, diethylene glycol monohexyl ether, propylene glycol methyl ether, propylene glycol ethyl ether, propylene glycol n-propyl ether, propylene glycol monobutyl ether, propylene glycol t-butyl ether, di- or tri-polypropylene glycol methyl or ethyl or propyl or butyl ether, acetate and propionate esters of glycol ethers. Short chain carboxylic acids include, but are not limited to, acetic acid, glycolic acid, lactic acid and propionic acid. Short chain esters include, but are not limited to, glycol acetate, and cyclic or linear volatile methylsiloxanes. Water insoluble solvents such as isoparafinic hydrocarbons, mineral spirits, alkylaromatics, terpenoids, terpenoid derivatives, terpenes, and terpenes derivatives can be mixed with a water soluble solvent when employed.

Examples of organic solvent having a vapor pressure less than 0.1 mm Hg (20° C.) include, but are not limited to, dipropylene glycol n-propyl ether, dipropylene glycol t-butyl ether, dipropylene glycol n-butyl ether, tripropylene glycol methyl ether, tripropylene glycol n-butyl ether, diethylene glycol propyl ether, diethylene glycol butyl ether, dipropylene glycol methyl ether acetate, diethylene glycol ethyl ether acetate, and diethylene glycol butyl ether acetate (all available from ARCO Chemical Company).

The solvents are preferably present at a level of from 0.001% to 10%, more preferably from 0.01% to 10%, most preferably from 1% to 4% by weight.

Additional Adjuncts

The cleaning compositions optionally contain one or more of the following adjuncts: stain and soil repellants, lubricants, odor control agents, perfumes, fragrances and fragrance release agents, brighteners, fluorescent whitening agents, and bleaching agents. Other adjuncts include, but are not limited to, acids, electrolytes, dyes and/or colorants, solubilizing materials, stabilizers, thickeners, defoamers, hydrotropes, cloud point modifiers, preservatives, and other polymers. The solubilizing materials, when used, include, but are not limited to, hydrotropes (e.g. water soluble salts of low molecular weight organic acids such as the sodium and/or potassium salts of toluene, cumene, and xylene sulfonic acid). The acids, when used, include, but are not limited to, organic hydroxy acids, citric acids, keto acid, and the like. Electrolytes, when used, include, calcium, sodium and potassium chloride. Thickeners, when used, include, but are not limited to, polyacrylic acid, xanthan gum, calcium carbonate, aluminum oxide, alginates, guar gum, methyl, ethyl, clays, and/or propyl hydroxycelluloses. Defoamers, when used, include, but are not limited to, silicones, aminosilicones, silicone blends, and/or silicone/hydrocarbon blends. Bleaching agents, when used, include, but are not limited to, peracids, hypohalite sources, hydrogen peroxide, and/or sources of hydrogen peroxide.

Preservatives, when used, include, but are not limited to, mildewstat or bacteriostat, methyl, ethyl and propyl parabens, short chain organic acids (e.g. acetic, lactic and/or glycolic acids), bisguanidine compounds (e.g. Dantagard and/or Glydant) and/or short chain alcohols (e.g. ethanol and/or IPA). The mildewstat or bacteriostat includes, but is not limited to, mildewstats (including non-isothiazolone compounds) include Kathon GC, a 5-chloro-2-methyl-4-isothiazolin-3-one, KATHON ICP, a 2-methyl-4-isothiazolin-3-one, and a blend thereof, and KATHON 886, a 5-chloro-2-methyl-4-isothiazolin-3-one, all available from Rohm and Haas Company; BRONOPOL, a 2-bromo-2-nitropropane 1,3 diol, from Boots Company Ltd., PROXEL CRL, a propyl-p-hydroxybenzoate, from ICI PLC; NIPASOL M, an o-phenyl-phenol, Na⁺ salt, from Nipa Laboratories Ltd., DOWICIDE A, a 1,2-Benzoisothiazolin-3-one, from Dow Chemical Co., and IRGASAN DP 200, a 2,4,4'-trichloro-2-hydroxydiphenylether, from Ciba-Geigy A.G.

Antimicrobial Agent

Antimicrobial agents include quaternary ammonium compounds and phenolics. Non-limiting examples of these quaternary compounds include benzalkonium chlorides and/or substituted benzalkonium chlorides, di($C_6$-$C_{14}$)alkyl di short chain ($C_{1-4}$ alkyl and/or hydroxyalkl) quaternaryammonium salts, N-(3-chloroallyl) hexaminium chlorides, benzethonium chloride, methylbenzethonium chloride, and cetylpyridinium chloride. Other quaternary compounds include the group consisting of dialkyldimethyl ammonium chlorides, alkyl dimethylbenzylammonium chlorides, dialkylmethylbenzylammonium chlorides, and mixtures thereof. Biguanide antimicrobial actives including, but not limited to polyhexamethylene biguanide hydrochloride, p-chlorophenyl biguanide; 4-chlorobenzhydryl biguanide, halogenated hexidine such as, but not limited to, chlorhexidine (1,1'-hexamethylene-bis-5-(4-chlorophenyl biguanide) and its salts are also in this class.

Builder/Buffer

The cleaning composition may include a builder or buffer, which increase the effectiveness of the surfactant. The builder or buffer can also function as a softener and/or a sequestering agent in the cleaning composition. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxysulfonates, and starch derivatives.

Builders or buffers can also include polyacetates and polycarboxylates. The polyacetate and polycarboxylate compounds include, but are not limited to, sodium, potassium, lithium, ammonium, and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These builders or buffers can also exist either partially or totally in the hydrogen ion form.

The builder agent can include sodium and/or potassium salts of EDTA and substituted ammonium salts. The substituted ammonium salts include, but are not limited to, ammonium salts of methylamine, dimethylamine, butylamine, butylenediamine, propylamine, triethylamine, trimethylamine, monoethanolamine, diethanolamine, triethanolamine, isopropanolamine, ethylenediamine tetraacetic acid and propanolamine.

Buffering and pH adjusting agents, when used, include, but are not limited to, organic acids, mineral acids, alkali metal and alkaline earth salts of silicate, metasilicate, polysilicate, borate, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2methylpropanol. Preferred buffering agents for compositions of this invention are nitrogen-containing materials. Some examples are amino acids such as lysine or lower alcohol amines like mono-, di-, and tri-ethanolamine.

Other preferred nitrogen-containing buffering agents are tri (hydroxymethyl)amino methane (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Other suitable buffers include ammonium carbamate, citric acid, acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide.

When employed, the builder, buffer, or pH adjusting agent comprises at least about 0.001% and typically about 0.01-5% of the cleaning composition. Preferably, the builder or buffer content is about 0.01-2%.

Effervescence

The cleaning composition may comprise materials which effervesce when combined with water. The materials may be within a water-soluble, water-insoluble, or water-dispersible pouch to slow the effervescent action or to protect the composition from premature hydration. The materials may comprise a polymeric agent to slow the effervescence. One component of the effervescent materials may be an acidic material. Suitable for this purpose are any acids present in dry solid form. Suitable for this purpose are C2-20 organic mono- and poly-carboxylic acids such as alpha- and beta-hydroxycarboxylic acids; C2-20 organophosphorus acids such as phytic acid; C2-20 organosulfur acids such as toluene sulfonic acid; and peroxides such as hydrogen peroxide or materials that generate hydrogen peroxide in solution. Typical hydroxycarboxylic acids include adipic, glutaric, succinic, tartaric, malic, maleic, lactic, salicylic and citric acids as well as acid forming lactones such as gluconolactone and gluccrolactone. A suitable acid is citric acid. Also suitable as acid material may be encapsulated acids. Typical encapsulating material may include water-soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7. These acids may also have a pH of less than 6.5 or less than 5. These acids may be at 25° C. in solid form, i.e. having melting points greater than 25° C. Concentrations of the acid should range from about 0.5 to about 80%, or from about 10 to about 65%, or from about 20 to about 45% by weight of the total composition.

Another component of the effervescent materials may be a alkaline material. The alkaline material may a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). An example of the alkaline material is sodium or potassium bicarbonate. Amounts of the alkaline material may range from about 1 to about 80%, or from about 5 to about 49%, or from about 15 to about 40%, or from about 25 to about 35% by weight of the total composition.

When the cleaning composition comprises effervescent materials, then the composition may comprise no more than 5%, or no more than 3.5%, or no more than 1% water by weight of the total composition. Water of hydration is not considered to be water for purposes of this calculation. However, water of hydration may be preferred or eliminated. The combined amount of acidic and alkaline materials may be greater than 1.5%, or from about 40 to about 95%, or from about 60 to about 80% by weight of the total composition.

Pine Oil, Terpene Derivatives and Essential Oils

Compositions according to the invention may comprise pine oil, terpene derivatives and/or essential oils. Pine oil, terpene derivatives and essential oils are used primarily for cleaning efficacy. They may also provide some antimicrobial efficacy and deodorizing properties. Pine oil, terpene derivatives and essential oils may be present in the compositions in amounts of up to about 1% by weight, preferably in amounts of 0.01% to 0.5% by weight.

Pine oil is a complex blend of oils, alcohols, acids, esters, aldehydes and other organic compounds. These include terpenes which include a large number of related alcohols or ketones. Some important constituents include terpineol. One type of pine oil, synthetic pine oil, will generally contain a higher content of turpentine alcohols than the two other grades of pine oil, namely steam distilled and sulfate pine oils. Other important compounds include alpha- and beta-pinene (turpentine), abietic acid (rosin), and other isoprene derivatives. Particularly effective pine oils are commercially available from Mellennium Chemicals, under the Glidco tradename. These pine oils vary in the amount of terpene alcohols and alpha-terpineol.

Terpene derivatives appropriate for use in the inventive composition include terpene hydrocarbons having a functional group, such as terpene alcohols, terpene ethers, terpene esters, terpene aldehydes and terpene ketones. Examples of suitable terpene alcohols include verbenol, transpinocarveol, cis-2-pinanol, nopol, isoborneol, carbeol, piperitol, thymol, alpha-terpineol, terpinen-4-ol, menthol, 1,8-terpin, dihydroterpineol, nerol, geraniol, linalool, citronellol, hydroxy-citronellol, 3,7-dimethyl octanol, dihydro-myrcenol, tetrahydro-alloocimenol, perillalcohol, and falcarindiol. Examples of suitable terpene ether and terpene ester solvents include 1,8-cineole, 1,4-cineole, isobornyl methylether, rose pyran, menthofuran, trans-anethole, methyl chavicol, allocimene diepoxide, limonene mono-epoxide, isobornyl acetate, nonyl acetate, terpinyl acetate, linalyl acetate, geranyl acetate, citronellyl acetate, dihydro-terpinyl acetate and meryl acetate. Further, examples of suitable terpene aldehyde and terpene ketone solvents include myrtenal, campholenic aldehyde, perillaldehyde, citronellal, citral, hydroxy citronellal, camphor, verbenone, carvenone, dihydro-carvone, carvone, piperitone, menthone, geranyl acetone, pseudo-ionone, ionine, iso-pseudo-methyl ionone, n-pseudo-methyl ionone, iso-methyl ionone and n-methyl ionone.

Essential oils include, but are not limited to, those obtained from thyme, lemongrass, citrus, lemons, oranges, anise, clove, aniseed, pine, cinnamon, geranium, roses, mint, lavender, citronella, eucalyptus, peppermint, camphor, sandalwood, rosmarin, vervain, fleagrass, lemongrass, ratanhiae, cedar and mixtures thereof. Preferred essential oils to be used herein are thyme oil, clove oil, cinnamon oil, geranium oil, eucalyptus oil, peppermint oil, mint oil or mixtures thereof.

Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salycilic acid, methyl salycilate, terpineol and mixtures thereof. Preferred actives of essential oils to be used herein are thymol, eugenol, verbenone, eucalyptol, terpineol, cinnamic acid, methyl salycilic acid, citric acid and/or geraniol.

Other essential oils include Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Canaga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin 69.degree. C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methhyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen. Each of these botanical oils is commercially available.

Particularly preferred oils include peppermint oil, lavender oil, bergamot oil (Italian), rosemary oil (Tunisian), and sweet orange oil. These may be commercially obtained from a variety of suppliers including: Givadan Roure Corp. (Clifton, N.J.); Berje Inc. (Bloomfield, N.J.); BBA Aroma Chemical Div. of Union Camp Corp. (Wayne, N.J.); Firmenich Inc. (Plainsboro N.J.); Quest International Fragrances Inc. (Mt. Olive Township, N.J.); Robertet Fragrances Inc. (Oakland, N.J.).

Particularly useful lemon oil and d-limonene compositions which are useful in the invention include mixtures of terpene hydrocarbons obtained from the essence of oranges, e.g., cold-pressed orange terpenes and orange terpene oil phase ex fruit juice, and the mixture of terpene hydrocarbons expressed from lemons and grapefruit.

Polymers

In suitable embodiments of the invention, polymeric material that changes the viscosity characteristics of the compositions is incorporated. For some combinations of cleaning compositions and substrates a thickener may be suitable. Thickeners, when used, include, but are not limited to, polyacrylic acid and copolymers, polysaccharide polymers, which include substituted cellulose materials like carboxymethylcellulose, ethyl cellulose, hydroxyethylcellulose, hydroxypropylcellulose, hydroxymethylcellulose, succinoglycan and naturally occurring polysaccharide polymers like xanthan gum, guar gum, locust bean gum, tragacanth gum or derivatives thereof.

In suitable embodiments of the invention, polymeric material that improves the hydrophilicity of the surface being treated is incorporated into the present compositions. The increase in hydrophilicity provides improved final appearance by providing "sheeting" of the water from the surface and/or spreading of the water on the surface, and this effect is preferably seen when the surface is rewetted and even when subsequently dried after the rewetting. Polymer substantivity is beneficial as it prolongs the sheeting and cleaning benefits. Another important feature of preferred polymers is lack of visible residue upon drying. In preferred embodiments, the polymer comprises 0.001 to 5%, preferably 0.01 to 1%, and most preferably 0.1 to 0.5% of the cleaning composition.

In general, the aqueous polymer containing composition may comprise a water-soluble or water dispersible polymer. The hydrophilic polymers preferably are attracted to surfaces and are absorbed thereto without covalent bonds. Examples of suitable polymers include the polymers and co-polymers of N,N dimethyl acrylamide, acrylamide, and certain monomers containing quaternary ammonium groups or amphoteric groups that favor substantivity to surfaces, along with co-monomers that favor adsorption of water, such as, for example, acrylic acid and other acrylate salts, sulfonates, betaines, and ethylene oxides.

With respect to the synthesis of the water soluble or water dispersible cationic copolymer, the level of the first monomer, which has a permanent cationic charge or that is capable of forming a cationic charge on protonation, is typically between 3 and 80 mol % and preferably 10 to 60 mol % of the copolymer. The level of second monomer, which is an acidic monomer that is capable of forming an anionic charge in the composition, when present is typically between 3 and 80 mol % and preferably 10 to 60 mol % of the copolymer. The level of the third monomer, which has an uncharged hydrophilic group, when present is typically between 3 and 80 mol % and preferably 10 to 60 mol % of the copolymer. When present, the level of uncharged hydrophobic monomer is less than about 50 mol % and preferably less than 10 mol % of the copolymer. The molar ratio of the first monomer to the second monomer typically ranges from 19:1 to 1:10 and preferably ranges from 9:1 to 1:6. The molar ratio of the first monomer to the third monomer is typically ranges from 4:1 to 1:4 and preferably ranges from 2:1 to 1:2.

The average molecular weight of the copolymer typically ranges from about 5,000 to about 10,000,000, with the preferred molecular weight range depending on the polymer composition with the proviso that the molecular weight is selected so that the copolymer is water soluble or water dispersible to at least 0.01% by weight in distilled water at 25° C.

Examples of permanently cationic monomers include, but are not limited to, quaternary ammonium salts of substituted acrylamide, methacrylamide, acrylate and methacrylate, such as trimethylammoniumethylmethacrylate, trimethylammoniumpropylmethacrylamide, trimethylammoniumethylmethacrylate, trimethylammoniumpropylacrylamide, 2-vinyl N-alkyl quaternary pyridinium, 4-vinyl N-alkyl quaternary pyridinium, 4-vinylbenzyltrialkylammonium, 2-vinyl piperidinium, 4-vinyl piperidinium, 3-alkyl 1-vinyl imidazolium, diallyldimethylammonium, and the ionene class of internal cationic monomers as described by D. R. Berger in *Cationic Surfactants, Organic Chemistry*, edited by J. M. Richmond, Marcel Dekker, New York, 1990, ISBN 0-8247-8381-6, which is incorporated herein by reference. This class includes co-poly ethylene imine, co-poly ethoxylated ethylene imine and co-poly quaternized ethoxylated ethylene imine, co-poly [(dimethylimino) trimethylene (dimethylimino) hexamethylene disalt], co-poly [(diethylimino) trimethylene (dimethylimino) trimethylene disalt], co-poly [(dimethylimino) 2-hydroxypropyl salt], co-polyquarternium-2, co-polyquarternium-17, and co-polyquarternium-18, as described in the *International Cosmetic Ingredient Dictionary*, 5th Edition, edited by J. A. Wenninger and G. N. McEwen, which is incorporated herein by reference. Other cationic monomers include those containing cationic sulfonium salts such as co-poly-1-[3-methyl-4-(vinyl-benzyloxy) phenyl]tetrahydrothiophenium chloride. Especially preferred monomers are mono- and di-quaternary derivatives of methacrylamide. The counterion of the cationic co-monomer can be selected from, for example, chloride, bromide, iodide, hydroxide, phosphate, sulfate, hydrosulfate, ethyl sulfate, methyl sulfate, formate, and acetate.

Examples of monomers that are cationic on protonation include, but are not limited to, acrylamide, N,N-dimethylacrylamide, N,N di-isopropylacryalmide, N-vinylimidazole, N-vinylpyrrolidone, ethyleneimine, dimethylaminohydroxypropyl diethylenetriamine, dimethylaminoethylmethacrylate, dimethylaminopropylmethacrylamide, dimethylaminoethylacrylate, dimethylaminopropylacrylamide, 2-vinyl pyridine, 4-vinyl pyridine, 2-vinyl piperidine, 4-vinylpiperidine, vinyl amine, diallylamine, methyldiallylamine, vinyl oxazolidone; vinyl methyoxazolidone, and vinyl caprolactam.

Monomers that are cationic on protonation typically contain a positive charge over a portion of the pH range of 2-11. Such suitable monomers are also presented in *Water-Soluble Synthetic Polymers: Properties and Behavior*, Volume II, by P. Molyneux, CRC Press, Boca Raton, 1983, ISBN 0-8493-6136. Additional monomers can be found in the *International Cosmetic Ingredient Dictionary*, 5th Edition, edited by J. A. Wenninger and G. N. McEwen, The Cosmetic, Toiletry, and Fragrance Association, Washington D.C., 1993, ISBN 1-882621-06-9. A third source of such monomers can be found in *Encyclopedia of Polymers and Thickeners for Cosmetics*, by R. Y. Lochhead and W. R. Fron, Cosmetics & Toiletries, vol. 108, May 1993, pp 95-135. All three references are incorporated herein.

Examples of acidic monomers that are capable of forming an anionic charge in the composition include, but are not limited to, acrylic acid, methacrylic acid, ethacrylic acid, dimethylacrylic acid, maleic anhydride, succinic anhydride, vinylsulfonate, cyanoacrylic acid, methylenemalonic acid, vinylacetic acid, allylacetic acid, ethylidineacetic acid, propylidineacetic acid, crotonic acid, fumaric acid, itaconic acid, sorbic acid, angelic acid, cinnamic acid, styrylacrylic acid, citraconic acid, glutaconic acid, aconitic acid, phenylacrylic acid, acryloxypropionic acid, citraconic acid, vinylbenzoic acid, N-vinylsuccinamidic acid, mesaconic acid, methacroylalanine, acryloylhydroxyglycine, sulfoethyl methacrylate, sulfopropyl acrylate, and sulfoethyl acrylate. Preferred acid monomers also include styrenesulfonic acid, 2-methacryloyloxymethane-1-sulfonic acid, 3-methacryloyloxypropane-1-sulfonic acid, 3-(vinyloxy)propane-1-sulfonic acid, ethylenesulfonic acid, vinyl sulfuric acid, 4-vinylphenyl sulfuric acid, ethylene phosphonic acid and vinyl phosphoric acid. Most preferred monomers include acrylic acid, methacrylic acid and maleic acid. The copolymers useful in this invention may contain the above acidic monomers and the alkali metal, alkaline earth metal, and ammonium salts thereof.

Examples of monomers having an uncharged hydrophilic group include but are not limited to vinyl alcohol, vinyl acetate, vinyl methyl ether, vinyl ethyl ether, ethylene oxide and propylene oxide. Especially preferred are hydrophilic esters of monomers, such as hydroxyalkyl acrylate esters, alcohol ethoxylate esters, alkylpolyglycoside esters, and polyethylene glycol esters of acrylic and methacrylic acid.

Finally, examples of uncharged hydrophobic monomers include, but are not limited to, $C_1$-$C_4$ alkyl esters of acrylic acid and of methacrylic acid.

The copolymers are formed by copolymerizing the desired monomers. Conventional polymerization techniques can be employed. Illustrative techniques include, for example, solution, suspension, dispersion, or emulsion polymerization. A preferred method of preparation is by precipitation or inverse suspension polymerization of the copolymer from a polymerization media in which the monomers are dispersed in a suitable solvent. The monomers employed in preparing the copolymer are preferably water soluble and sufficiently soluble in the polymerization media to form a homogeneous solution. They readily undergo polymerization to form polymers which are water-dispersable or water-soluble. The preferred copolymers contain acrylamide, methacrylamide and substituted acrylamides and methacrylamides, acrylic and methacrylic acid and esters thereof. Suitable synthetic methods for these copolymers are described, for example, in Kirk-Othmer, *Encyclopedia of Chemical Technology*, Volume 1, Fourth Ed., John Wiley & Sons.

Other examples of polymers that provide the sheeting and anti-spotting benefits are polymers that contain amine oxide hydrophilic groups. Polymers that contain other hydrophilic groups such a sulfonate, pyrrolidone, and/or carboxylate groups can also be used. Examples of desirable poly-sulfonate polymers include polyvinylsulfonate, and more preferably polystyrene sulfonate, such as those sold by Monomer-Polymer Dajac (1675 Bustleton Pike, Feasterville, Pa. 19053). A typical formula is as follows: $[CH(C_6H_4SO_3Na)-CH_2]_n-CH(C_6H_5)-CH_2$ wherein n is a number to give the appropriate molecular weight as disclosed below.

Typical molecular weights are from about 10,000 to about 1,000,000, preferably from about 200,000 to about 700,000. Preferred polymers containing pyrrolidone functionalities include polyvinyl pyrrolidone, quaternized pyrrolidone derivatives (such as Gafquat 755N from International Specialty Products), and co-polymers containing pyrrolidone, such as polyvinylpyrrolidone/dimethylaminoethylmethacrylate (available from ISP) and polyvinyl pyrrolidone/acrylate (available from BASF). Other materials can also provide substantivity and hydrophilicity including cationic materials that also contain hydrophilic groups and polymers that contain multiple ether linkages. Cationic materials include cationic sugar and/or starch derivatives and the typical block copolymer detergent surfactants based on mixtures of polypropylene oxide and ethylene oxide are representative of the polyether materials. The polyether materials are less substantive, however.

Preferred polymers comprise water-soluble amine oxide moieties. It is believed that the partial positive charge of the amine oxide group can act to adhere the polymer to the surface of the surface substrate, thus allowing water to "sheet" more readily. To the extent that polymer anchoring promotes better "sheeting" higher molecular materials are preferred. Increased molecular weight improves efficiency and effectiveness of the amine oxide-based polymer. The preferred polymers of this invention have one or more monomeric units containing at least one N-oxide group. At least about 10%, preferably more than about 50%, more preferably greater than about 90% of said monomers forming said polymers contain an amine oxide group. These polymers can be described by the general formula: P(B) wherein each P is selected from homopolymerizable and copolymerizable moieties which attach to form the polymer backbone, preferably vinyl moieties, e.g. $C(R)2$--$C(R)2$, wherein each R is H, C1-C12 (preferably C.sub.1-C.sub.4) alkyl(ene), C6-C12 aryl(ene) and/or B; B is a moiety selected from substituted and unsubstituted, linear and cyclic C1-C12 alkyl, C1-C12 alkylene, C1-C12 heterocyclic, aromatic C6-C12 groups and wherein at least one of said B moieties has at least one amine oxide group present; u is from a number that will provide at least about 10% monomers containing an amine oxide group to about 90%; and t is a number such that the average molecular weight of the polymer is from about 2,000 to about 500,000, preferably from about 5,000 to about 250,000, and more preferably from about 7,500 to about 200,000. Preferred polymers also include poly(4-vinylpyridine N-oxide) polymers (PVNO), wherein the average molecular weight of the polymer is from about 2,000 to about 500,000 preferably from about 5,000 to about 400,000, and more preferably from about 7,500 to about 300,000. In general, higher molecular weight polymers are preferred. Often, higher molecular weight polymers allow for use of lower levels of the wetting polymer, which can provide benefits in floor cleaner applications. The desirable molecular weight range of polymers useful in the present invention stands in contrast to that found in the art relating to polycarboxylate, polystyrene sulfonate, and polyether based additives, which prefer molecular weights in the range of 400,000 to 1,500,000. Lower molecular weights for the preferred poly-amine oxide polymers of the present invention are due to greater difficulty in manufacturing these polymers in higher molecular weight.

Some non-limiting examples of homopolymers and copolymers which can be used as water soluble polymers of the present invention are: adipic acid/dimethylaminohydroxypropyl diethylenetriamine copolymer; adipic acid/epoxypropyl diethylenetriamine copolymer; polyvinyl alcohol; methacryloyl ethyl betaine/methacrylates copolymer; ethyl acrylate/methyl methacrylate/methacrylic acid/acrylic acid copolymer; polyamine resins; and polyquaternary amine resins; poly(ethenylformamide); poly(vinylamine) hydrochloride; poly(vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride). Preferably, said copolymer and/or homopolymers are selected from the group consisting of adipic acid/dimethylaminohydroxypropyl diethylenetriamine copolymer; poly(vinylpyrrolidone/dimethylaminoethyl methacrylate); polyvinyl alcohol; ethyl acrylate/methyl methacrylate/ethacrylic acid/acrylic acid copolymer; methacryloyl ethyl betaine/methacrylates copolymer; polyquaternary amine resins; poly(ethenylformamide); poly(vinylamine) hydrochloride; poly(vinyl alcohol-co-6% vinylamine); poly(vinyl alcohol-co-12% vinylamine); poly(vinyl alcohol-co-6% vinylamine hydrochloride); and poly(vinyl alcohol-co-12% vinylamine hydrochloride).

Polymers useful in the present invention can be selected from the group consisting of copolymers of hydrophilic monomers. The polymer can be linear random or block copolymers, and mixtures thereof. The term "hydrophilic" is used herein consistent with its standard meaning of having affinity for water. As used herein in relation to monomer units and polymeric materials, including the copolymers, "hydrophilic" means substantially water-soluble. In this regard, "substantially water soluble" shall refer to a material that is soluble in distilled (or equivalent) water, at 25° C., at a concentration of about 0.2% by weight, and are preferably soluble at about 1% by weight. The terms "soluble", "solubility" and the like, for purposes hereof, correspond to the maximum concentration of monomer or polymer, as applicable, that can dissolve in water or other solvents to form a homogeneous solution, as is well understood to those skilled in the art.

Nonlimiting examples of useful hydrophilic monomers are unsaturated organic mono- and polycarboxylic acids, such as acrylic acid, methacrylic acid, crotonic acid, malieic acid and its half esters, itaconic acid; unsaturated alcohols, such as vinyl alcohol, allyl alcohol; polar vinyl heterocyclics, such as, vinyl caprolactam, vinyl pyridine, vinyl imidazole; vinyl amine; vinyl sulfonate; unsaturated amides, such as acrylamides, e.g., N,N-dimethylacrylamide, N-t-butyl acrylamide; hydroxyethyl methacrylate; dimethylaminoethyl methacrylate; salts of acids and amines listed above; and the like; and mixtures thereof. Some preferred hydrophilic monomers are acrylic acid, methacrylic acid, N,N-dimethyl acrylamide, N,N-dimethyl methacrylamide, N-t-butyl acrylamide, dimethylamino ethyl methacrylate, thereof, and mixtures thereof.

Polycarboxylate polymers are those formed by polymerization of monomers, at least some of which contain carboxylic functionality. Common monomers include acrylic acid, maleic acid, ethylene, vinyl pyrrolidone, methacrylic acid, methacryloylethylbetaine, etc. Preferred polymers for substantivity are those having higher molecular weights. For example, polyacrylic acid having molecular weights below about 10,000 are not particularly substantive and therefore do not normally provide hydrophilicity for three rewettings with all compositions, although with higher levels and/or certain surfactants like amphoteric and/or zwitterionic detergent surfactants, molecular weights down to about 1000 can provide some results. In general, the polymers should have molecular weights of more than about 10,000, preferably more than about 20,000, more preferably more than about 300,000, and even more preferably more than about 400,000. It has also been found that higher molecular weight polymers, e.g., those having molecular weights of more than about 3,000,000, are extremely difficult to formulate and are less effective in providing anti-spotting benefits than lower molecular weight polymers. Accordingly, the molecular weight should normally be, especially for polyacrylates, from about 20,000 to about 3,000,000; preferably from about 20,000 to about 2,500,000; more preferably from about 300,000 to about 2,000,000; and even more preferably from about 400,000 to about 1,500,000.

Non-limiting examples of polymers for use in the present invention include the following: poly(vinyl pyrrolidone/acrylic acid) sold under the name "Acrylidone"® by ISP and poly(acrylic acid) sold under the name "Accumer"® by Rohm & Haas. Other suitable materials include sulfonated polystyrene polymers sold under the name Versaflex® sold by National Starch and Chemical Company, especially Versaflex 7000. The level of polymeric material will normally be less than about 0.5%, preferably from about 0.001% to about 0.4%, more preferably from about 0.01% to about 0.3%. In general, lower molecular weight materials such as lower molecular weight poly(acrylic acid), e.g., those having molecular weights below about 10,000, and especially about 2,000, do not provide good anti-spotting benefits upon rewetting, especially at the lower levels, e.g., about 0.02%. One should use only the more effective materials at the lower levels. In order to use lower molecular weight materials, substantivity should be increased, e.g., by adding groups that provide improved attachment to the surface, such as cationic groups, or the materials should be used at higher levels, e.g., more than about 0.05%.

Nanoparticles

Nanoparticles, defined as particles with diameters of about 400 nm or less, are technologically significant, since they are utilized to fabricate structures, coatings, and devices that have novel and useful properties due to the very small dimensions of their particulate constituents. "Non-photoactive" nanoparticles do not use UV or visible light to produce the desired effects. Nanoparticles can have many different particle shapes. Shapes of nanoparticles can include, but are not limited to spherical, parallelpiped-shaped, tube shaped, and disc or plate shaped.

Nanoparticles with particle sizes ranging from about 2 nm to about 400 nm can be economically produced. Particle size distributions of the nanoparticles may fall anywhere within the range from about 1 nm, or less, to less than about 400 nm, alternatively from about 2 nm to less than about 100 nm, and alternatively from about 2 nm to less than about 50 nm. For example, a layer synthetic silicate can have a mean particle size of about 25 nanometers while its particle size distribution can generally vary between about 10 nm to about 40 nm. Alternatively, nanoparticles can also include crystalline or amorphous particles with a particle size from about 1, or less, to about 100 nanometers, alternatively from about 2 to about 50 nanometers. Nanotubes can include structures up to 1 centimeter long, alternatively with a particle size from about 1 nanometer, or less, to about 50 nanometers. Nanoparticles can be present from 0.01 to 1%.

Inorganic nanoparticles generally exist as oxides, silicates, carbonates and hydroxides. These nanoparticles are generally hydrophilic. Some layered clay minerals and inorganic metal oxides can be examples of nanoparticles. The layered clay minerals suitable for use in the coating composition include those in the geological classes of the smectites, the kaolins, the illites, the chlorites, the attapulgites and the mixed layer clays. Smectites include montmorillonite, bentonite, pyrophyllite, hectorite, saponite, sauconite, nontronite, talc, beidellite, volchonskoite and vermiculite. Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

The layered clay minerals suitable for use in the coating composition may be either naturally occurring or synthetic. An example of one embodiment of the coating composition uses natural or synthetic hectorites, montmorillonites and bentonites. Another embodiment uses the hectorites clays commercially available. Typical sources of commercial hectorites are LAPONITE® from Southern Clay Products, Inc., U.S.A; Veegum Pro and Veegum F from R. T. Vanderbilt, U.S.A.; and the Barasyms, Macaloids and Propaloids from Baroid Division, National Read Comp., U.S.A.

The inorganic metal oxides used in the coating composition may be silica- or alumina-based nanoparticles that are naturally occurring or synthetic. Aluminum can be found in many naturally occurring sources, such as kaolinite and bauxite. The naturally occurring sources of alumina are processed by the Hall process or the Bayer process to yield the desired alumina type required. Various forms of alumina are commercially available in the form of Gibbsite, Diaspore, and Boehmite from manufacturers such as Condea.

Synthetic hectorites, such as LAPONITE RD®, do not contain any fluorine. An isomorphous substitution of the hydroxyl group with fluorine will produce synthetic clays referred to as sodium magnesium lithium fluorosilicates. These sodium magnesium lithium fluorosilicates, marketed as LAPONITE B® and LAPONITE S®, contain fluoride ions of greater than 0% up to about 8%, and preferably about 6% by weight. LAPONITE B® particles are flat disc-shaped, or plate shaped, and have a mean particle size of about 40 nanometers in diameter and about 1 nanometer in thickness. Another variant, called LAPONITE S®, contains about 6% of tetrasodium polyphosphate as an additive. In some instances, LAPONITE B® by itself is believed, without wishing to be bound to any particular theory, to be capable of providing a more uniform coating (that is, more continuous, i.e., less openings in the way the coating forms after drying), and can provide a more substantive (or durable) coating than some of the other grades of LAPONITE® by themselves (such as LAPONITE RD®).

The aspect ratio for disk shaped nanoparticles is the ratio of the diameter of the clay particle to that of the thickness of the clay particle. The aspect ratio of individual particles of LAPONITE® B is approximately 40 and the aspect ratio of individual particles of LAPONITE® RD is approximately 25. A high aspect ratio is desirable for film formation of nanosized clay materials. More important to the invention is the aspect ratio of the dispersed particles in a suitable carrier medium, such as water. The aspect ratio of the particles in a dispersed medium can be considered to be lower where several of the disc shaped particles are stacked on top of one another than in the case of individual particles. The aspect ratio of dispersions can be adequately characterized by TEM (transmission electron microscopy).

LAPONITE B® occurs in dispersions as essentially single clay particles or stacks of two or fewer clay particles. The LAPONITE RD® occurs essentially as stacks of two or more single clay particles. Thus, the aspect ratio of the particles dispersed in the carrier medium can be dramatically different from the aspect ratio of single disc-shaped particle. The aspect ratio of LAPONITE B® is about 20-40 and the aspect ratio of LAPONITE RD® is less than 15.

In some preferred embodiments, the nanoparticles will have a net excess charge on one of their dimensions. For instance, flat plate-shaped nanoparticles may have a positive charge on their flat surfaces, and a negative charge on their edges. Alternatively, such flat plate-shaped nanoparticles may have a negative charge on their flat surfaces and a positive charge on their edges. Preferably, the nanoparticles have an overall net negative charge. This is believed to aid in hydrolilizing the surface coated with the nanoparticles. The amount of charge, or "charge density", on the nanoparticles can be measured in terms of the mole ratio of magnesium oxide to lithium oxide in the nanoparticles. In preferred embodiments, the nanoparticles have a mole ratio of magnesium oxide to lithium oxide of less than or equal to about 11%.

Depending upon the application, the use of variants and isomorphous substitutions of LAPONITE® provides great flexibility in engineering the desired properties of the coating composition used in the present invention. The individual platelets of LAPONITE® are negatively charged on their faces and possess a high concentration of surface bound water. When applied to a hard surface, the hard surface is hydrophilically modified and exhibits surprising and significantly improved wetting and sheeting, quick drying, uniform drying, anti-spotting, anti-soil deposition, cleaner appearance, enhanced gloss, enhanced color, minor surface defect repair, improved smoothness, anti-hazing properties, modification of surface friction, reduced damage to abrasion and improved transparency properties. In addition, the LAPONITE® modified surface exhibits "self-cleaning" properties (dirt removal via water rinsing, e.g. from rainwater) and/or soil release benefits (top layers are strippable via mild mechanical action).

In contrast to hydrophilic modification with organic polymers, the benefits provided by nanoparticles, such as LAPONITE®, either alone or in combination with a charged modifier, are longer lived. For example, sheeting/anti-spotting benefits are maintained on an automobile body and glass window after multiple rinses versus the duration of such benefits after only about one rinse with tap water or rainwater on a surface coated with hydrophilic polymer technology.

Substances Generally Recognized as Safe

Compositions according to the invention may comprise substances generally recognized as safe (GRAS), including essential oils, oleoresins (solvent-free) and natural extractives (including distillates), and synthetic flavoring materials and adjuvants. Compositions may also comprise GRAS materials commonly found in cotton, cotton textiles, paper and paperboard stock dry food packaging materials (referred herein as substrates) that have been found to migrate to dry food and, by inference may migrate into the inventive compositions when these packaging materials are used as substrates for the inventive compositions.

Suitable GRAS materials are listed in the Code of Federal Regulations (CFR) Title 21 of the United States Food and Drug Administration, Department of Health and Human Services, Parts 180.20, 180.40 and 180.50, which are hereby incorporated by reference. These suitable GRAS materials include essential oils, oleoresins (solvent-free), and natural extractives (including distillates). The GRAS materials may be present in the compositions in amounts of up to about 10% by weight, preferably in amounts of 0.01 and 5% by weight.

Preferred GRAS materials include oils and oleoresins (solvent-free) and natural extractives (including distillates) derived from alfalfa, allspice, almond bitter (free from prussic acid), ambergris, ambrette seed, angelica, angostura (cusparia bark), anise, apricot kernel (persic oil), asafetida, balm (lemon balm), balsam (of Peru), basil, bay leave, bay (myrcia oil), bergamot (bergamot orange), bois de rose (Aniba rosaeodora Ducke), cacao, camomile (chamomile) flowers, cananga, capsicum, caraway, cardamom seed (cardamon), carob bean, carrot, cascarilla bark, cassia bark, Castoreum, celery seed, cheery (wild bark), chervil, cinnamon bark, Civet (zibeth, zibet, zibetum), ceylon (*Cinnamomum zeylanicum Nees*), cinnamon (bark and leaf), citronella, citrus peels, clary (clary sage), clover, coca (decocainized), coffee, cognac oil (white and green), cola nut (kola nut), coriander, cumin (cummin), curacao orange peel, cusparia bark, dandelion, dog grass (quackgrass, triticum), elder flowers, estragole (esdragol, esdragon, estragon, tarragon), fennel (sweet), fenugreek, galanga (galangal), geranium, ginger, grapefruit, guava, hickory bark, horehound (hoarhound), hops, horsemint, hyssop, immortelle (*Helichrysum augustifolium DC*), jasmine, juniper (berries), laurel berry and leaf, lavender, lemon, lemon grass, lemon peel, lime, linden flowers, locust bean, lupulin, mace, mandarin (*Citrus reticulata Blanco*), marjoram, mate, menthol (including menthyl acetate), molasses (extract), musk (Tonquin musk), mustard, naringin, neroli (bigarade), nutmeg, onion, orange (bitter, flowers, leaf, flowers, peel), origanum, palmarosa, paprika, parsley, peach kernel (persic oil, pepper (black, white), peanut (stearine), peppermint, Peruvian balsam, petitgrain lemon, petitgrain mandarin (or tangerine), pimenta, pimenta leaf, pipsissewa leaves, pomegranate, prickly ash bark, quince seed, rose (absolute, attar, buds, flowers, fruit, hip, leaf), rose geranium, rosemary, safron, sage, St. John's bread, savory, schinus molle (*Schinus molle L*), sloe berriers, spearmint, spike lavender, tamarind, tangerine, tarragon, tea (*Thea sinensis L.*), thyme, tuberose, turmeric, vanilla, violet (flowers, leaves), wild cherry bark, ylang-ylang and zedoary bark.

Suitable synthetic flavoring substances and adjuvants are listed in the Code of Federal Regulations (CFR) Title 21 of the United States Food and Drug Administration, Department of Health and Human Services, Part 180.60, which is hereby incorporated by reference. These GRAS materials may be present in the compositions in amounts of up to about 1% by weight, preferably in amounts of 0.01 and 0.5% by weight.

Suitable synthetic flavoring substances and adjuvants that are generally recognized as safe for their intended use, include acetaldehyde (ethanal), acetoin (acetyl methylcarbinol), anethole (parapropenyl anisole), benzaldehyde (benzoic aldehyde), n-Butyric acid (butanoic acid), d- or l-carvone (carvol), cinnamaldehyde (cinnamic aldehyde), citral (2,6-dimethyloctadien-2,6-al-8, gera-nial, neral), decanal (N-decylaldehyde, capraldehyde, capric aldehyde, caprinaldehyde, aldehyde C-10), ethyl acetate, ethyl butyrate, 3-Methyl-3-phenyl glycidic acid ethyl ester (ethyl-methyl-phenyl-glycidate, so-called strawberry aldehyde, C-16 aldehyde), ethyl vanillin, geraniol (3,7-dimethyl-2,6 and 3,6-octadien-1-ol), geranyl acetate (geraniol acetate), limonene (d-, l-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin) and vanillin.

Suitable GRAS substances that may be present in the inventive compositions that have been identified as possibly migrating to food from cotton, cotton textiles, paper and paperboard materials used in dry food packaging materials are listed in the Code of Federal Regulations (CFR) Title 21 of the United States Food and Drug Administration, Department of Health and Human Services, Parts 180.70 and 180.90, which are hereby incorporated by reference. The GRAS materials may be present in the compositions either by addition or incidentally owing to migration from the substrates to the compositions employed in the invention, or present owing to both mechanisms. If present, the GRAS materials may be present in the compositions in amounts of up to about 1% by weight.

Suitable GRAS materials that are suitable for use in the invention, identified as originating from either cotton or cotton textile materials used as substrates in the invention, include beef tallow, carboxymethylcellulose, coconut oil (refined), cornstarch, gelatin, lard, lard oil, oleic acid, peanut oil, potato starch, sodium acetate, sodium chloride, sodium silicate, sodium tripolyphosphate, soybean oil (hydrogenated), talc, tallow (hydrogenated), tallow flakes, tapioca starch, tetrasodium pyrophosphate, wheat starch and zinc chloride.

Suitable GRAS materials that are suitable for use in the invention, identified as originating from either paper or paperboard stock materials used as substrates in the invention, include alum (double sulfate of aluminum and ammonium potassium, or sodium), aluminum hydroxide, aluminum oleate, aluminum palmitate, casein, cellulose acetate, cornstarch, diatomaceous earth filler, ethyl cellulose, ethyl vanillin, glycerin, oleic acid, potassium sorbate, silicon dioxides, sodium aluminate, sodium chloride, sodium hexametaphosphate, sodium hydrosulfite, sodium phosphoaluminate, sodium silicate, sodium sorbate, sodium tripolyphosphate, sorbitol, soy protein (isolated), starch (acid modified, pregelatinized and unmodified), talc, vanillin, zinc hydrosulfite and zinc sulfate.

Fragrance

Compositions of the present invention may comprise from about 0.01% to about 50% by weight of the fragrance oil. Compositions of the present invention may comprise from about 0.2% to about 25% by weight of the fragrance oil. Compositions of the present invention may comprise from about 1% to about 25% by weight of the fragrance oil.

As used herein the term "fragrance oil" relates to the mixture of perfume raw materials that are used to impart an overall pleasant odor profile to a composition. As used herein the term "perfume raw material" relates to any chemical compound which is odiferous when in an un-entrapped state, for example in the case of pro-perfumes, the perfume component is considered, for the purposes of this invention, to be a perfume raw material, and the pro-chemistry anchor is considered to be the entrapment material. In addition "perfume raw materials" are defined by materials with a ClogP value preferably greater than about 0.1, more preferably greater than about 0.5, even more preferably greater than about 1.0. As used herein the term "ClogP" means the logarithm to base 10 of the octanol/water partition coefficient. This can be readily calculated from a program called "CLOGP" which is available from Daylight Chemical Information Systems Inc., Irvine Calif., U.S.A. Octanol/water partition coefficients are described in more detail in U.S. Pat. No. 5,578,563.

The individual perfume raw materials which comprise a known natural oil can be found by reference to Journals commonly used by those skilled in the art such as "Perfume and Flavourist" or "Journal of Essential Oil Research". In addition some perfume raw materials are supplied by the fragrance houses as mixtures in the form of proprietary speciality accords. In order that fragrance oils can be developed with the appropriate character for the present invention the perfume raw materials have been classified based upon two key physical characteristics:

(i) boiling point (BP) measured at 1 atmosphere pressure. The boiling point of many fragrance materials are given in Perfume and Flavor Chemicals (Aroma Chemicals), Steffen Arctander (1969). Perfume raw materials for use in the present invention are divided into volatile raw materials (which have a boiling point of less than, or equal to, about 250° C.) and residual raw materials (which have a boiling point of greater than about 250° C., preferably greater than about 275° C.). All perfume raw materials will preferably have boiling points (BP) of about 500° C. or lower.

(ii) odour detection threshold which is defined as the lowest vapour concentration of that material which can be olfactorily detected. The odour detection threshold and some odour detection threshold values are discussed in e.g., "Standardized Human Olfactory Thresholds", M. Devos et al, IRL Press at Oxford University Press, 1990, and "Compilation of Odor and Taste Threshold Values Data", F. A. Fazzalar, editor ASTM Data Series DS 48A, American Society for Testing and Materials, 1978, both of said publications being incorporated by reference. Perfume raw materials for use in the present invention can be classified as those with a low odour detection threshold of less than 50 parts per billion, preferably less than 10 parts per billion and those with a high odour detection threshold which are detectable at greater than 50 parts per billion (values as determined from the reference above).

Since, in general, perfume raw materials refer to a single individual compound, their physical properties (such ClogP, boiling point, odour detection threshold) can be found by referencing the texts cited above. In the case that the perfume raw material is a natural oil, which comprises a mixture of several compounds, the physical properties of the complete oil should be taken as the weighted average of the individual components. In the case that the perfume raw material is a proprietary speciality accord the physical properties should be obtain from the Supplier.

In general a broad range of suitable perfume raw materials can be found in U.S. Pat. Nos. 4,145,184, 4,209,417, 4,515,705, and 4,152,272. Non-limiting examples of perfume raw materials which are useful for blending to formulate fragrance oils for the present invention are given below. Any perfume raw materials, natural oils or proprietary speciality accords known to a person skilled in the art can be used within the present invention.

Volatile perfume raw materials useful in the present invention are selected from, but are not limited to, aldehydes with a relative molecular mass of less than or equal to about 200, esters with a relative molecular mass of less than or equal to about 225, terpenes with a relative molecular mass of less than or equal to about 200, alcohols with a relative molecular mass of less than or equal to about 200 ketones with a relative molecular mass of less than or equal to about 200, nitriles, pyrazines, and mixtures thereof.

Examples of volatile perfume raw materials having a boiling point of less than, or equal to, 250° C., with a low odor detection are selected from, but are not limited to, anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials having a boiling point of less than, or equal to, 250° C., which are generally known to have a low odour detection threshold include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, iso propyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, c is 1,3-oxathiane-2-methyl-4-propyl.

Other volatile perfume raw materials having a boiling point of less than, or equal to, 250° C., which are useful in the present invention, which have a high odor detection threshold, are selected from, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

Examples of residual "middle and base note" perfume raw materials having a boiling point of greater than 250° C., which have a low odor detection threshold are selected from, but are not limited to, ethyl methyl phenyl glycidate, ethyl vanillin, heliotropin, indol, methyl anthranilate, vanillin, amyl salicylate, coumarin. Further examples of residual perfume raw materials having a boiling point of greater than 250° C. which are generally known to have a low odour detection threshold include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxylphenyl butanone, 8-cyclohexadecen-1-one, oxocyclohexadecen-2-one/habanolide, florhydral, intreleven aldehyde.

Other residual "middle and base note" perfume raw materials having a boiling point of greater than 250° C. which are useful in the present invention, but which have a high odour detection threshold, are selected from, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Entrapment Material

Compositions of the present invention comprise an entrapment material preferably at a level of from about 0.1% to about 95%, preferably from about 0.5% to about 50%, more preferably from about 1% to about 25% and even more preferably from about 2% to about 8%, by weight, of an entrapment material.

As defined herein an "entrapment material" is any material which, after application of the composition to a substrate, suppresses the volatility of the perfume raw materials within the fragrance oil thus delaying their evaporation. It is not necessary that the entrapment material forms an association with the perfume raw material within the composition itself, only that this association exists on the substrate after application of the composition. Non-limiting examples of mechanisms by which the delay in evaporation may occur are by the entrapment material reversibly or irreversibly, physically or chemically associating with the perfume raw material through complexing, encapsulating, occluding, absorbing, binding, or otherwise adsorbing the perfume raw materials of the fragrance oil.

As defined herein "reversible entrapment" means that any entrapment material: perfume raw material association in which the association can be broken down so that the entrapment material and perfume raw materials are released from each other. As defined herein "irreversible entrapment" means that the entrapment material: perfume raw material association cannot be broken down. As defined herein "chemically associated" means that the entrapment material and perfume raw material are linked through a covalent, ionic, hydrogen or other type of chemical bond. As defined herein "physically associated" means that the entrapment material and perfume raw material are linked through a bond with a weaker force such as a Van der Waals force. Highly preferred is that, upon the substrate, the entrapment material and the perfume raw material form a reversible physical or chemical association.

As defined herein "to delay the evaporation of a perfume raw material" means to slow down or inhibit the evaporation rate of said perfume raw material from the substrate such that the fragrance "top note" character of the perfume raw material is detectable for at least 2 hours after application to the substrate.

Entrapment materials for use herein are selected from polymers; capsules, microcapsules and nanocapsules; liposomes; pro-perfumes selected from more than 1 type of pro-chemistry; film formers; absorbents; cyclic oligosaccharides and mixtures thereof. Preferred are pro-perfumes selected from more than 1 type of pro-chemistry, absorbents and cyclic oligosaccharides and mixtures thereof. Highly preferred are cyclic oligosaccharides.

Within the entrapment association it is preferred that the weight ratio of top note perfume raw material to entrapment material within the associated form is in the range from about 1:20 to about 20:1, more preferably in the range from about 1:10 to about 10:1, even more preferably in the range from about 1:10 to about 1:4.

It is highly preferred for compositions of the present invention that the entrapment material reversibly, chemically and physically complexes the perfume raw materials. Non limiting, and preferred, examples of entrapment materials that can act in this way are cyclic oligosaccharides, or mixtures of 5 different cyclic oligosaccharides.

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to α, β and γ respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substitutent or mixture of substitutents. Herein the use of the term "mixture of substitutents" means that two or more different suitable substitutents can be substituted onto one cyclic oligosaccharide. The derivatives of cyclodextrins consist mainly of molecules wherein some of the OH groups have been substituted. Suitable substitutents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino)propyl ether; quaternary ammonium groups; anionic cyclodextrins such as carboxyalkyl groups, sulphobutylether groups, sulphate groups, and succinylates; amphoteric cyclodextrins; and mixtures thereof. Other cyclodextrin derivatives are disclosed in copending U.S. application Ser. No. 09/32192 (May 27, 1999), all of which are incorporated herein by reference.

The substitutents may be saturated or unsaturated, straight or branched chain. Preferred substitutents include saturated and straight chain alkyl groups, hydroxyalkyl groups and mixtures thereof. Preferred alkyl and hydroxyalkyl substitutents are selected from C1-C8 alkyl or hydroxyalkyl groups or mixtures thereof, more preferred alkyl and hydroxyalkyl substitutents are selected from C1-C6 alkyl or hydroxyalkyl groups or mixtures thereof, even more preferred alkyl and hydroxyalkyl substitutents are selected from C1-C4 alkyl or hydroxyalkyl groups and mixtures thereof. Especially preferred alkyl and hydroxyalkyl substitutents are propyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl substitutents. Therefore, preferred examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin. Most preferred examples of cyclic oligosaccharides for use herein are methyl-α-cyclodextrin and methyl-β-cyclodextrin. These are available from Wacker-Chemie GmbH Hanns-Seidel-Platz 4, Munchen, DE under the tradename Alpha W6 M and Beta W7 M respectively. Especially preferred is methyl-β-cyclodextrin.

Methods of modifying cyclic oligosaccharides are well known in the art. For example, see "*Methods of Selective Modifications of Cyclodextrins*" Chemical Reviews (1998) Vol. 98, No. 5, pp 1977-1996, Khan et al and U.S. Pat. No. 5,710,268.

In addition to preferred substitutents themselves, it is also preferred that the cyclic oligosaccharides of the compositions used for the present invention have an average degree of substitution of at least 1.6, wherein the term "degree of substitution" means the average number of substitutents per saccharide unit. Preferred cyclic oligosaccharides for use herein have an average degree of substitution of less than about 2.8. More preferably the cyclic oligosaccharides for use herein have an average degree of substitution of from about 1.7 to about 2.0. The average number of substitutents can be determined using common Nuclear Magnetic Resonance techniques known in the art.

The cyclic oligosaccharides of the compositions used for the present invention are preferably soluble in both water and ethanol. As used herein "soluble" means at least about 0.1 g of solute dissolves in 100 ml of solvent, at 25° C. and 1 atm of pressure. Preferably the cyclic oligosaccharides for use herein have a solubility of at least about 1 g/100 ml, at 25° C. and 1 atm of pressure. Preferred is that cyclic oligosaccharides are only present at levels up to their solubility limits in a given composition at room temperature. A person skilled in the art will recognise that the levels of cyclic oligosaccharides used in the present invention will also be dependent on the components of the composition and their levels, for example the solvents used or the exact fragrance oils, or combination of fragrance oils, present in the composition. Therefore, although the limits stated for the entrapment material are preferred, they are not exhaustive.

Encapsulation Using Capsules, Micro-Capsules and Nano-capsules

Encapsulation of fragrances within capsules, micro-capsules or nanaocapsules which are broken down by environmental triggers can be used to reduce the volatility of fragrance oils by surrounding the oil by small droplets as a resistant wall. This may be either water sensitive or insensitive. In the first case the fragrance is released when the encapsulated particle is affected by moisture loss from the skin; while in the second case the capsule wall must be ruptured mechanically before the fragrance is released. Encapsulation techniques are well known in the art including DE 1,268,316; U.S. Pat. Nos. 3,539,465; 3,455,838.

Moisture sensitive capsules, micro-capsules and nanocapsules are preferably formed from, but not limited to, a polysaccharide polymer. Examples of suitable polymers are dextrins, especially low-viscosity dextrins including maltodextrins. A particularly preferred example of a low viscosity dextrin is one which, as a 50% dispersion in water has a viscosity at 25° C., using a Brookfield Viscometer fitted with an "A" type T-Bar rotating at 20 rpm in helical mode, of 330±20 mPa.s. This dextrin is known as Encapsul 855 and is available from National Starch and Chemicals Ltd. A further example of a polysaccharide that can be used to form the moisture sensitive capsules is gum acacia.

Time release micro-capsules are also suitable for use in compositions of the present invention for entrapping hydrophobic perfume raw materials. Such compositions comprise the perfume raw materials encapsulated in a wax or polymer matrix which in turn is coated with a compatible surfactant.

The wax or polymers used to form the matrix have a melting point in the range from about 35° C. to about 120° C. at 1 atmosphere pressure. These are described in detail in EP-A-908,174.

Film formers can also be used to reduce the volatility profile of perfume raw materials. When the fragrance is applied to a substrate, such as the skin, it is believed that film formers entrap the perfume oils during the evaporation of the volatile solvent thus hindering the release of the volatile material. Any film former which is compatible with the perfume raw materials may be used, preferably the film former will be soluble in water-ethanol mixture. Film former materials useful in this invention include, but are not limited to, ionic and non-ionic derivatives of water soluble polymers. Examples of suitable film forming materials are water soluble polymers containing a cationic moiety such as polyvinyl pyrrolidine and its derivatives having a molecular weight of 50,000 to 1,000,000. Other examples of ionic polymeric film forming materials are cationic cellulose derivatives sold under the trade names of Polymer JR (union Carbide), Klucel GM (hercules) and ethoxylated polyethyleneimine sold under the trade name PEI 600 (Dow). Examples of suitable cellulosic derivatives such as hydroxymethyl cellulose, hydroxypropyl methylcellulose and hydroxyethyl cellulose. Another examples of film formers is benzophenone. Non limiting examples of film forming materials are given in U.S. Pat. No. 3,939,099.

Additional non-limiting examples of other polymer systems that can be used include water soluble anionic polymers e.g., polyacrylic acids and their water-soluble salts are useful in the present invention to delay the evaporation rate of certain amine-type odours. Preferred polyacrylic acids and their alkali metal salts have an average molecular weight of less than about 20,000, preferably less than 10,000, more preferably from about 500 to about 5,000. Polymers containing sulphonic acid groups, phosphoric acid groups, phosphonic acid groups and their water soluble salts, and their mixtures thereof, and mixtures with carboxylic acid and carboxylate groups, are also suitable.

Water soluble polymers containing both cationic and anionic functionalities are also suitable. Examples of these polymers are given in U.S. Pat. No. 4,909,986. Another example of water-soluble polymers containing both cationic and anionic functionalities is a copolymer of dimethyldiallyl ammonium chloride and acrylic acid, commercially available under the trade name Merquat 280® from Calgon.

Synthesising pro-perfumes or pro-fragrances from perfume raw materials can result in compounds which impart a delayed release mechanism to that specific perfume raw material. Pro-perfumes useful within the present invention include those selected from more than 1 type of pro-chemistry which ensures that a wide range of possible perfume raw materials can be used. This is consistent with the objective of providing unique fragrances with a broad spectrum of "top note" characters.

Within a pro-perfume the perfume raw material has been reacted with more than one type of chemical groups such as acetal, ketal, ester, hydrolysable inorganic-organic. As such, as defined within the present invention, the perfume raw material is considered to constitute part of the fragrance oil and the chemical groups to constitute part of the entrapment material. Pro-perfumes themselves are designed to be non-volatile, or else have a very low volatility. However, once on the substrate, the perfume raw material is released from the pro-perfume. Once released the perfume raw material has its original characteristics. The perfume raw material may be released from the pro-perfume in a number of ways. For example, it may be released as a result of simple hydrolysis, or by shift in an equilibrium reaction or by a pH-change, or by enzymatic release. The fragrances herein can be relatively simple in their compositions, comprising a single chemical, or can comprise highly sophisticated complex mixtures of natural and synthetic chemical components, all chosen to provide any desired odor. Non-limiting pro-perfumes suitable for use in the present application are described in WO 98/47477, WO 99/43667, WO 98/07405, WO 98/47478.

When clarity of solution is not needed, odour absorbing materials such as zeolites and/or activated carbon can be used to modify the release rate of perfume raw materials. A preferred class of zeolites is characterised as "intermediate" silicate/aluminate zeolites. The intermediate zeolites are characterised by $SiO_2/AlO_2$ molar ratios of less than about 10, preferably in the range from about 2 to about 10. The intermediate zeolites have an advantage over the "high" zeolites since they have an affinity for amine-type odors, they are more weight efficient for odor absorption since they have a larger surface area and they are more moisture tolerant and retain more of their odour absorbing capacity in water than the high zeolites. A wide variety of intermediate zeolites suitable for use herein are commercially available as Valfor® CP301-68, Valfor® 300-63, Valfor® CP300-35 and Valfor® 300-56 available from PQ Corporation, and the CBV100® series of zeolites from Conteka. Zeolite materials marketed under the trade name Abscents® and Smellrite® available from The Union Carbide Corporation and UOP are also preferred. These materials are typically available as a white powder in the 3-5 cm particle size range. Such materials are preferred over the intermediate zeolites for control of sulphur containing odours e.g., thiols, mercaptans.

Carbon materials suitable for use in the present invention are materials well known in commercial practice as absorbents for organic molecules and/or for air purification purposes. Often, such carbon material is referred to as "activated" carbon or "activated charcoal". Such carbon is available from commercial sources under trade names as; Calgon-Type CPG®; Type PCB®; Type SGL®; Type CAL®; and Type OL®. Other odor absorbers suitable for use herein include silica molecular sieves, activated alumina, bentonite and kaolonite.

The fragrance may contain a volatile solvent. As used herein, "volatile" refers to substances with a significant amount of vapour pressure under ambient conditions, as is understood by those in the art. The volatile solvents for use herein will preferably have a vapour pressure of about 2 kPa or more, more preferably about 6 kPa or more at 25° C. The volatile solvents for use herein will preferably have a boiling point under 1 atm, of less than about 150° C., more preferably less than about 100° C., even more preferably less than about 90° C., even more preferably still less than about 80° C.

Preferably the volatile solvents for use herein will be safe for use on a wide range of substrates, more preferably on human or animal skin or hair. Suitable volatile solvents include, but are not limited to, those found in the *CTFA International Cosmetic Ingredient Dictionary and Handbook,* 7th edition, volume 2 P1670-1672, edited by Wenninger and McEwen (The Cosmetic, Toiletry, and Fragrance Association, Inc., Washington, D.C., 1997). Conventionally used volatile solvents include C3-C14 saturated and unsaturated, straight or branched chain hydrocarbons such as cyclohexane, hexane, heptane, isooctane, isopentane, pentane, toluene, xylene; halogenated alkanes such as perfluorodecalin; ethers such as dimethyl ether, diethyl ether; straight or branched chain alcohols and diols such as methanol, ethanol, propanol, isopropanol, n-butyl alcohol, t-butyl alcohol, benzyl alcohol, butoxypropanol, butylene glycol, isopentyldiol; aldehydes and ketones such as acetone; volatile silicones such as cyclomethicones for example octamethyl cyclo tetrasiloxane and decamethyl cyclopentane siloxane; volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane; propellants, and mixtures thereof. Preferred volatile solvents are ethers such as dimethyl ether, diethyl ether; straight or branched chain alcohols and diols such as methanol, ethanol, propanol, isopropanol, n-butyl alcohol, t-butyl alcohol, benzyl alcohol, butoxypropanol, butylene glycol, isopentyldiol; volatile silicones such as cyclomethicones for example octamethyl cyclo tetrasiloxane and decamethyl cyclopentane siloxane; propellants, and mixtures thereof. More preferred for use herein are C1-C4 straight chain or branched chain alcohols for example methanol, ethanol, propanol, isopropanol and butanol and mixtures thereof, and most preferred for use herein is ethanol.

The fragrance component may also comprise "nonvolatile" solvents. Suitable non-volatile solvents include, but are not limited to, benzyl benzoate, diethyl phthalate, isopropyl myristate, and mixtures thereof.

When cyclic oligosaccharides are present in the compositions of the present invention, low molecular weight polyol molecular wedge having from about 2 to about 12 carbon atoms, preferably from about 2 to about 6 carbon atoms and at least one —OH functional group, preferably at least 2 -OH functional groups are preferably used herein for further prolonging the fragrance character of the composition. These polyols can further contain ether groups within the carbon chain. Suitable examples include ethylene glycol, propylene glycol, dipropylene glycol, 1,4-butanediol, 1,6-hexanediol and mixtures thereof. When present these polyols are present at a level of from about 0.01% to about 20%, preferably from about 0.1% to about 10%, and especially from about 0.5% to about 5% by weight of composition. It is preferred that the molar ratio of molecular wedge material to oligosaccharide is from 10:1 to 1:10, preferably 1:1 or greater, especially 1:1.

Compositions and fragrance oils for use in the present invention should be prepared according to procedures usually used in and that are well known and understood by those skilled in the art with materials of similar phase partitioning can be added in any order. The entrapment of the perfume raw materials can occur at any reasonable stage in the preparation of the overall composition. As such the fragrance oil can be prepared in its entirety, then entrapped with a suitable material before addition to the remainder of the composition. Alternatively the entrapment material can be added to the balance of the composition prior to addition of the complete fragrance oil. Finally it is possible to entrap any single perfume raw material, or group of raw materials, individually before either adding these to the balance of the fragrance oil or to the balance of the composition. Preparation of specific fragrance compositions is described in US2003/0211125.

Water

Since the composition is an aqueous composition, water can be, along with the solvent, a predominant ingredient. The water should be present at a level of less than 99.9%, more preferably less than about 99%, and most preferably, less than about 98%. The water may be deionized, industrial soft water, or any suitable grade or water. Where the cleaning composition is concentrated, the water may be present in the composition at a concentration of less than about 85 wt. %.

Method of Use

The wipe or cleaning pad can be used for cleaning, disinfectancy, or sanitization on inanimate, household surfaces, including floors, counter tops, furniture, windows, walls, and automobiles. Other surfaces include stainless steel, chrome, and shower enclosures. The wipe or cleaning pad can be packaged individually or together in canisters, tubs, etc. The package may contain information printed on said package comprising a instruction to use the more abrasive side to remove soil followed by using the less abrasive side to wipe the soil away. The wipe or cleaning pad can be used with the hand, or as part of a cleaning implement attached to a tool or motorized tool, such as one having a handle. Examples of tools using a wipe or pad include U.S. Pat. No. 6,611,986 to Seals, WO00/71012 to Belt et al., U.S. Pat. App. 2002/0129835 to Pieroni and Foley, and WO00/27271 to Policicchio et al.

EXAMPLES

Examples of suitable cleaning compositions are provided in Tables I and II. The cleaning compositions can be loaded on the cleaning substrate in a ratio of from 0.2 to 3.0 of cleaning composition to cleaning substrate. The cleaning compositions can be loaded on the cleaning substrate in a ratio of from 1.0 to 2.0 of cleaning composition to cleaning substrate. The pH of the cleaning composition can be measured by adding 5 g of the composition to 100 g of water.

TABLE I

|  | Example A | Example B | Example C | Example D | Example E |
|---|---|---|---|---|---|
| Alkyl polyglycoside[a] | 2.0 | 5.5 |  | 13.8 | 10.2 |
| Alcohol ethoxylate[b] |  | 1.5 | 9.7 |  |  |
| Sodium dodecyl diphenyloxide disulfonate[c] | 0.5 |  |  | 2.6 |  |
| Sodium lauryl sulfate[d] | 4.5 | 1.3 |  | 2.6 | 2.5 |
| Glycolic acid |  | 2.1 | 6.1 | 8.1 |  |
| Citric acid |  |  |  |  | 1.5 |
| Lactic acid | 4.0 |  |  |  |  |
| Sulfamic acid | 1.0 |  |  |  |  |
| Isopropanol |  |  |  |  | 0.5 |

TABLE I-continued

|                              | Example A | Example B | Example C | Example D | Example E |
|------------------------------|-----------|-----------|-----------|-----------|-----------|
| Dipropylene glycol n-butyl ether[e] | 2.0       |           |           |           |           |
| d-limonene                   |           |           |           |           | 0.5       |
| Blue Dye                     |           |           |           | 0.006     | 0.006     |
| Fragrance                    | 1.5       |           | 0.5       | 1.00      |           |
| Water                        | balance   | balance   | balance   | balance   | balance   |
| PH                           |           |           |           | 2.2       |           |

[a] APG 325N from Cognis
[b] Alfonic 1012-5 from Vista Chemical
[c] Dowfax 2A1 from Dow Chemical
[d] Stepanol WAC from Stepan Chemical
[e] Dowanol DPnB from Dow Chemical

TABLE II

|                                | Example F | Example G | Example H | Example I | Example J |
|--------------------------------|-----------|-----------|-----------|-----------|-----------|
| Alkyl polyglycoside            | 6.3       | 13.0      | 10.0      | 10.0      | 5.0       |
| Alcohol ethoxylate             |           | 2.0       |           |           | 2.0       |
| Sodium secondary alkane sulfonate[f] | 28.0 | 2.0       |           |           |           |
| Sodium sulfosuccinate[g]       |           |           | 5.0       |           |           |
| Sodium lauryl sulfate          |           | 3.0       |           | 3.0       | 3.0       |
| Alkanolamide[h]                | 4.0       |           |           |           |           |
| Citric acid                    | 4.0       | 50.0      | 1.0       | 5.0       |           |
| Sulfamic acid                  |           |           |           |           | 4.0       |
| Hydrogen peroxide              |           |           |           |           | 2.0       |
| Sodium bicarbonate             |           | 25.0      |           |           |           |
| Hydrophilic polymer[i]         |           |           | 1.0       |           |           |
| Nanoparticle[j]                |           |           |           | 4.0       |           |
| Fragrance                      | 0.2       | 1.0       |           | 1.0       | 0.5       |
| Preservative                   |           |           |           |           |           |
| 2-Benzyl-4-chlorophenol[k]     |           |           | 1.0       |           |           |
| Thickener[l]                   |           |           | 0.5       |           |           |
| Cyclodextrin[m]                |           |           |           | 3.0       |           |
| Water                          | balance   |           |           |           |           |
| PH                             |           |           |           | 2.2       |           |

[f] Hostapur SAS from Clariant
[g] Gerapon SDS from Rhodia
[h] Ninol 11 CM from Stepan Chemical
[i] Alco from Alco Chemical
[j] Laponite B from Southern Clay Producs
[k] Nipacide BCP 50 from Clariant
[l] Kelsan S from Kelco
[m] Cavasol from Wacher A substrate (Example AA) was prepared by glue lamination of three nonwoven layers. The surface scrubbing layer was formed from needle punched polypropylene (25%-18 denier, 30% 1.5 denier, 45% 3 denier) with a singe finish and reinforced with spunbond 10 gsm polypropylene. The total basis weight of the surface scrubbing layer was 100 gsm. The middle reservoir layer consisted of a 4 layer ultrasonically bonded structure (top and bottom layers—polyester (6, 9 denier), carded web forming with chemical bonding, 78 gsm; middle two layers—polypropylene (2 denier), spunbond, 75 gsm). The total basis weight of the middle reservoir layer was 313 gsm. The bottom layer consisted of bicomponent fiber (polyethylene/polyester (3,6 denier)) made by carded web forming, through air bonded. The total basis weight of the bottom layer was 146 gsm. The substrate can be directly attached to a cleaning implement or attached first to a fitment and then to a cleaning implement.

Sanitizer Test. Six grams of the cleaning composition from Example D impregnated onto a substrate pad which was made as described above in Example AA. Prior to use, each substrate pad was wetted for a count of three seconds in 2 L of tap water. The pad was attached to a cleaning implement and wiped across a shower door. The substrate was rewetted as needed on visual cues of fewer bubbles and/or lacking in wetness. A total of 44 square feet on surface was cleaned. After each test, the substrate while still on the cleaning implement was used to perform a sanitizer test. The substrate was used to wipe the contaminated glass carrier back-and-forth a total of 8 times. The contact time was 5 minutes with a 5% soil load added to the bacterial suspension. Following the contact time, the individual carriers were neutralized in 20 mL of D/E broth. Additionally, the substrate was neutralized in 300 mL of D/E broth. After shaking and stomachering respectively, serial dilution and pour plating methods were performed to enumerated each samples. Samples were plated in duplicate at $10^0$, $10^{-1}$ and $10^{-2}$. Control material (substrate with no active) was also tested in the same manner, after wetting and cleaning the glass door. All appropriate controls were performed. All controls, plates and other material was incubated at 35 to 37° C. for 2 days, then refrigerated prior to counting. The cleaning substrates gave greater than 99.9% reduction of S. aureus on PVC and glazed ceramic tiles.

The substrate prepared in the sanitizer test above was stored for 1 week at room temperature. After storage, the substrate contained no visible liquid on the outside of the pad and was dry-to-the-touch.

Six grams of the cleaning composition from Example D impregnated onto a substrate pad which was made as described above in Example AA. The substrate with the cleaning composition was attached to a cleaning implement and then submerged in water and used to clean shower walls. During the cleaning process the blue appearance of the substrate from the blue dye completely disappeared.

The cleaning composition from Example G was impregnated onto a cleaning substrate. The substrate with the cleaning composition was attached to a cleaning implement and then submerged in water and used to clean shower walls. The cleaning substrate provided effervescence during cleaning.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A process of cleaning a surface using a cleaning implement with a disposable substrate attached to a fitment and impregnated with a cleaning composition comprising the steps of:
   a. attaching the disposable substrate having a plastic rigid fitment to the cleaning implement;
   b. wetting the disposable substrate; and
   c. scrubbing the surface;
   d. wherein the cleaning composition comprises:
      1. an alkyl sulfate surfactant; and
      2. 10 to 65% of sulfamic acid wherein the composition has a pH of 2.2 or less.

2. The process of claim 1, wherein the composition additionally comprises glycolic acid.

3. The process of claim 1, wherein the composition additionally comprises lactic acid.

4. The process of claim 1, wherein the surface is the surface of a shower.

5. The process of claim 1, wherein the surface is the surface of a toilet.

6. A process of cleaning a surface using a cleaning implement with a disposable substrate impregnated with a cleaning composition comprising the steps of:
   a. attaching the disposable substrate having a rigid plastic fitment attaching means to the cleaning implement;
   b. wetting the disposable substrate; and
   c. scrubbing the surface;
   d. wherein the cleaning composition comprises:
      1. an alkyl sulfate surfactant; and
      2. 20 to 45% of sulfamic acid and an acid selected from the group consisting of glycolic acid, lactic acid and combinations thereof wherein the composition has a pH of 2.2 or less.

7. The process of claim 6, wherein the composition comprises glycolic acid.

8. The process of claim 6, wherein the composition comprises lactic acid.

9. A process of cleaning a surface using a cleaning implement with a disposable substrate impregnated with a cleaning composition comprising the steps of:
   a. attaching the nonwoven web disposable substrate having a plastic rigid fitment attaching means to the cleaning implement having a clamping means so that the disposable substrate is not attached directly to the cleaning implement wherein the clamping means is a gripping mechanism and wherein the gripping mechanism is an integral part of the handle of the cleaning implement;
   b. wetting the disposable substrate; and
   c. scrubbing the surface;
   d. wherein the cleaning composition comprises:
      1. an alkyl sulfate surfactant; and
      2. 10 to 65% sulfamic acid wherein the composition has a pH of 2.2 or less.

10. The process of claim 9, wherein the composition comprises 20 to 45% of the acid.

11. The process of claim 9, wherein the composition additionally comprises glycolic acid.

12. The process of claim 9, wherein the surfactant additionally comprises an alkyl polyglycoside surfactant.

13. The process of claim 9, wherein the surfactant further comprises an alkyldiphenyloxide disulfonate.

* * * * *